(12) United States Patent
Koyama et al.

(10) Patent No.: US 9,366,401 B2
(45) Date of Patent: Jun. 14, 2016

(54) LIGHTING SYSTEM

(75) Inventors: Isamu Koyama, Saitama (JP); Takeshi Tanaka, Hiroshima (JP); Shuro Hayashi, Hiroshima (JP)

(73) Assignee: LIMITED LIABILITY COMPANY JAPAN MEDICAL CREATIVE, Saitama (JP)

( * ) Notice: Subject to any disclaimer, the term of this patent is extended or adjusted under 35 U.S.C. 154(b) by 350 days.

(21) Appl. No.: 13/054,310

(22) PCT Filed: Jul. 15, 2009

(86) PCT No.: PCT/JP2009/003348
§ 371 (c)(1),
(2), (4) Date: Mar. 18, 2011

(87) PCT Pub. No.: WO2010/007785
PCT Pub. Date: Jan. 21, 2010

(65) Prior Publication Data
US 2011/0160541 A1  Jun. 30, 2011

(30) Foreign Application Priority Data
Jul. 15, 2008  (JP) .................................. 2008-183359

(51) Int. Cl.
*A61B 1/06* (2006.01)
*F21L 14/00* (2006.01)
(Continued)

(52) U.S. Cl.
CPC ............. *F21L 14/00* (2013.01); *A61B 19/5202* (2013.01); *F21L 2/00* (2013.01); *F21V 21/084* (2013.01);
(Continued)

(58) Field of Classification Search
CPC ...................... A61B 19/5202; A61B 2019/262; A61B 1/0692; F21V 21/084; F21V 33/0068; A61C 1/088

USPC .......... 600/212, 223, 241, 247–249; 362/572, 362/573, 105–107, 804
See application file for complete search history.

(56) References Cited

U.S. PATENT DOCUMENTS 2,539,104 A * 1/1951 Rodel ............................ 600/248
2,893,379 A * 7/1959 Springer ....................... 600/184
(Continued)

FOREIGN PATENT DOCUMENTS

| JP | 3022512 U | 12/1995 |
| JP | 3098051 U | 9/2003 |

(Continued)

OTHER PUBLICATIONS

International Search Report for PCT/JP2009/003348 dated Aug. 18, 2009.
(Continued)

*Primary Examiner* — Matthew Lawson
(74) *Attorney, Agent, or Firm* — Nixon Peabody LLP; Joseph Bach, Esq.

(57) ABSTRACT

The lighting system 1 includes a light emitting unit 4 including light emitting diodes, and a securing member 5 for securing the light emitting unit 4 to a head of a healthcare worker. The radiation of light from the light emitting unit 4 eliminates the need for a shadowless lamp. When the light emitting unit 4 is fixed to the head, the light emitting unit 4 moves with the movement of the healthcare worker, and furthermore, when the healthcare worker moves his or her head, the direction of light radiation can be changed as desired. The use of an auxiliary lighting unit 6 and a camera 22 can provide safe surgery.

4 Claims, 20 Drawing Sheets

(51) Int. Cl.
*A61B 19/00* (2006.01)
*F21L 2/00* (2006.01)
*F21V 21/08* (2006.01)
*F21V 21/084* (2006.01)
*F21V 21/30* (2006.01)
*F21V 29/02* (2006.01)
*F21V 31/03* (2006.01)
*F21Y 101/02* (2006.01)

(52) U.S. Cl.
CPC ............ *F21V 21/0824* (2013.01); *F21V 21/30* (2013.01); *A61B 2019/262* (2013.01); *A61B 2019/521* (2013.01); *F21V 29/02* (2013.01); *F21V 31/03* (2013.01); *F21Y 2101/02* (2013.01)

(56) References Cited

U.S. PATENT DOCUMENTS

| | | | | | |
|---|---|---|---|---|---|
| 4,234,910 | A | * | 11/1980 | Price | G02B 6/0008 351/158 |
| 5,722,762 | A | * | 3/1998 | Soll | 362/105 |
| 6,877,875 | B2 | * | 4/2005 | Yu et al. | 362/105 |
| 6,908,208 | B1 | * | 6/2005 | Hyde et al. | 362/105 |
| 7,192,151 | B2 | * | 3/2007 | Clupper et al. | 362/105 |
| 7,699,486 | B1 | * | 4/2010 | Beiner | G02C 11/04 351/158 |
| 7,871,375 | B2 | * | 1/2011 | Talieh | 600/249 |
| 8,408,735 | B2 | * | 4/2013 | Kretschmann | 362/231 |
| 2003/0067769 | A1 | * | 4/2003 | Gilpin | 362/184 |
| 2003/0095781 | A1 | * | 5/2003 | Williams | 385/146 |
| 2004/0143167 | A1 | * | 7/2004 | Branch et al. | 600/212 |
| 2004/0264193 | A1 | | 12/2004 | Okumura | |
| 2005/0099824 | A1 | * | 5/2005 | Dowling et al. | 362/572 |
| 2005/0194876 | A1 | | 9/2005 | Shimada et al. | |
| 2005/0195599 | A1 | * | 9/2005 | Marka | 362/232 |
| 2007/0097702 | A1 | * | 5/2007 | Crowder | 362/570 |
| 2008/0002402 | A1 | * | 1/2008 | Mandikos | 362/231 |
| 2008/0144305 | A1 | * | 6/2008 | Medinis | 362/105 |
| 2009/0122536 | A1 | | 5/2009 | Scholz | |
| 2009/0216088 | A1 | * | 8/2009 | Danna et al. | 600/212 |
| 2009/0227847 | A1 | * | 9/2009 | Tepper et al. | 600/249 |
| 2011/0105851 | A1 | * | 5/2011 | Horvath | 600/249 |
| 2012/0209079 | A1 | * | 8/2012 | McMahon et al. | 600/223 |

FOREIGN PATENT DOCUMENTS

| | | |
|---|---|---|
| JP | 2005-058440 A | 3/2005 |
| JP | 2005-211409 A | 8/2005 |
| JP | 2005-279255 A | 10/2005 |
| JP | 2005-304599 A | 11/2005 |
| JP | 2006-147482 A | 6/2006 |
| JP | 2009-502377 A | 1/2009 |
| WO | WO 03-019072 A1 | 3/2003 |
| WO | WO 2007-014629 A1 | 2/2007 |

OTHER PUBLICATIONS

Office Action for Japanese Patent Application No. 2010-520778 dated Apr. 1, 2014.

* cited by examiner

LIGHTING SYSTEM

RELATED APPLICATIONS

This application is a National Phase of International Application No. PCT/JP2009/003348, entitled "LIGHTING DEVICE", which was filed on Jul. 15, 2009, and which claims priority of Japanese Patent Application No. 2008-183359, filed on Jul. 15, 2008, and the disclosures of which are hereby incorporated by reference herein in their entirety.

TECHNICAL FIELD

The present invention relates to lighting systems used when healthcare workers provide medical treatment, such as surgery.

BACKGROUND ART

Typically, a shadowless lamp for preventing a shadow from being cast over a surgical field is placed, as a lighting system illuminating the surgical field, in an operating room (see, e.g., PATENT DOCUMENT 1). The shadowless lamp includes a lamp unit including many lamps, and the lamp unit is usually attached to the ceiling of an operating room through a movable mechanism. The shadowless lamp is used while the location of the lamp unit is adjusted as required by a doctor actually performing a procedure.

CITATION LIST

PATENT DOCUMENT 1: Japanese Patent Publication No. 2006-147482

SUMMARY OF THE INVENTION

Technical Problem

However, since such a shadowless lamp is configured such that many lamps are attached to a ceiling through a movable mechanism, the entire shadowless lamp forms a large-scale heavy fixture, and thus, the ceiling needs to be reinforced, etc.

Heat is generated from the lamps of the lamp unit, and thus, cooling for reducing the increase in indoor temperature is expensive.

Since the many lamps are lighted, the amount of power consumption is large.

When a doctor moves during surgery, and thus, the lamp unit is located behind the doctor, light from the lamp unit is blocked by the doctor, thereby darkening a surgical field. Therefore, the location of the lamp unit must be changed. In this case, the doctor typically instructs an assistant to change the location of the lamp unit, and the assistant adjusts the location of the lamp unit, thereby requiring such an assistant for adjusting the location of the lamp unit, and thus, increasing the labor cost.

Furthermore, the lamp unit is attached to a ceiling, and thus, if, e.g., bacteria-laden dust falls from the lamp unit and the movable mechanism during the movement of the lamp unit for adjusting the location of the lamp unit, the dust might adhere to a patient immediately below the lamp unit, and the patient might acquire an infection. In order to prevent such a situation, the lamp unit and the movable mechanism need to be cleaned and sterilized, thereby requiring maintenance.

As described above, the cost of introducing such a shadowless lamp is high.

In addition, when such an assistant adjusts the location of the lamp unit, a person who provides an instruction to change the location and a person who adjusts the location are different, and thus, it is difficult to locate the lamp unit as desired by the doctor. This may cause the doctor to feel stress.

The present invention has been made in view of the foregoing point, and it is an object of the present invention to enable introduction of a lighting system for use during medical treatment performed by a healthcare worker at low cost and enable change of the direction of light radiation as desired by the healthcare worker without causing dust, etc., to fall.

Solution to the Problem

In order to achieve the above object, a lighting system according to a first aspect of the invention includes: a light emitting unit; and a securing member for securing the light emitting unit to a head of a healthcare worker.

According to this configuration, the light emitting unit is fixed to the head of the healthcare worker during medical treatment, thereby achieving reliable illumination from a location close to a target without using a large-scale lighting system, such as a shadowless lamp, including many lamp units. This eliminates the need for, e.g., reinforcing the ceiling, and can reduce the cooling cost and power consumption. Since a lamp unit and a movable mechanism are not required, this eliminates the need for cleaning and sterilizing the lamp unit and the movable mechanism.

Since the light emitting unit is fixed to the head of the healthcare worker during illumination, the light emitting unit moves with the movement of the healthcare worker, and furthermore, when the healthcare worker moves his or her head, the direction of light radiation can be changed as desired by the healthcare worker. Since the light emitting unit moves only with the movement of the healthcare worker, dust, etc., is much less likely to fall to a patient.

A second aspect of the invention is directed to the lighting system of the first aspect of the invention, wherein the light emitting unit includes a white light emitting diode and a red light emitting diode.

Specifically, when illuminating human tissue with the white light emitting diode, white is emphasized to the human eye, thereby making it difficult to accurately recognize, e.g., blood vessels, etc., during surgery. However, when the light emitting unit includes the red light emitting diode, this can prevent white from becoming prominently visible, thereby setting the color reproducibility and color rendering suitable for observing the human tissue. Since the light intensity in a red region of the spectrum of light emitted from the light emitting unit increases, this reduces glare from light reflected off, e.g., a surgical instrument.

A third aspect of the invention is directed to the lighting system of the first or second aspect of the invention, wherein the light emitting unit includes at least one of a green light emitting diode and a blue light emitting diode.

This configuration allows the spectrum of light emitted from the light emitting unit to be closer to the spectrum of natural light.

A fourth aspect of the invention is directed to the lighting system of any one of the first through third aspect of the invention, wherein the light emitting unit includes a light emitting diode configured to emit an infrared ray.

With this configuration, human tissue is irradiated with infrared rays. Therefore, for example, when human tissue is photographed using an infrared thermography camera, the temperature distribution of the tissue can be obtained as an image.

A fifth aspect of the invention is directed to the lighting system of the second or third aspect of the invention, wherein the light emitting unit includes a connector to and from which the light emitting diodes are attachable and removable.

With this configuration, when a light emitting diode emitting a specific color is disconnected from the connector, and the connector is equipped with a light emitting diode emitting another color, this enables change of the color reproducibility and color rendering. Furthermore, the brightness level can be changed by reducing the number of light emitting diodes.

A sixth aspect of the invention is directed to the lighting system of any one of the first through fifth aspects of the invention further including: an auxiliary lighting unit placed in a thoracic cavity or abdominal cavity of a human.

With this configuration, when, e.g., the thoracic cavity or abdominal cavity is operated, the interior of the thoracic cavity or abdominal cavity can be directly illuminated.

A seventh aspect of the invention is directed to the lighting system of the sixth aspect of the invention, wherein a protector for protecting a wound region formed by incising body surface tissue of the human is fitted with the auxiliary lighting unit.

With this configuration, when the protector over the wound region is fitted with the auxiliary lighting unit, the auxiliary lighting unit can be fixed without, e.g., causing damage to human tissue.

An eighth aspect of the invention is directed to the lighting system of the sixth aspect of the invention, wherein the auxiliary lighting unit includes a needle configured so as to be inserted into human tissue.

With this configuration, when the needle of the auxiliary lighting unit is inserted into tissue in the thoracic cavity or abdominal cavity, the auxiliary lighting unit can be fixed at an optional location.

A ninth aspect of the invention is directed to the lighting system of the first aspect of the invention further including: an illumination angle changer for changing an illumination angle of light.

With this configuration, the illumination angle of light from the light emitting unit can be changed depending on the procedure and the operator.

Advantages of the Invention

According to the first aspect of the invention, the light emitting unit is fixed to the head of the healthcare worker, thereby reliably illuminating a necessary region without using a shadowless lamp, and introducing the lighting system at low cost. Since a shadowless lamp is not required, this prevents bacteria-laden dust, etc., from falling to a patient, thereby preventing the patient from acquiring an infection. Furthermore, since the light emitting unit can be moved with the movement of the healthcare worker, the direction of light radiation can be changed as desired by the healthcare worker, thereby preventing the healthcare worker from feeling stress during medical treatment.

The lighting system of the present invention can reliably illuminate a necessary region from a location close to the necessary region, thereby performing medical treatment in an outpatient treatment room, a cardiac catheterization room, an emergency room, etc., without a shadowless lamp.

According to the second aspect of the invention, the light emitting unit includes the white light emitting diode and the red light emitting diode, and thus, when illuminating human tissue with the light emitting unit, the color reproducibility and color rendering can be set suitable for observing human tissue. This enables blood vessels, etc., to be accurately recognized, thereby improving the safety of medical treatment. Since the light emitting unit includes the red light emitting diode, this reduces glare from light reflected off, e.g., a surgical instrument, and thus, reduces the strain on the eyes of the healthcare worker, resulting in a reduction in fatigue.

According to the third aspect of the invention, the light emitting unit includes at least one of the green light emitting diode and the blue light emitting diode. This allows light emitted from the light emitting unit to be closer to natural light, and thus, reduces the strain on the eyes of the healthcare worker, resulting in a reduction in fatigue.

According to the fourth aspect of the invention, the light emitting diode emitting an infrared ray is provided. Therefore, the temperature distribution of tissue can be obtained as an image by using an infrared thermography camera. The locations and shapes of blood vessels, the amount of blood flowing through blood vessels, etc., are recognized based on the obtained temperature distribution image, thereby helping medical treatment.

According to the fifth aspect of the invention, the light emitting diodes are attachable and removable. This facilitates changing the color reproducibility and color rendering and changing the brightness level.

According to the sixth aspect of the invention, the auxiliary lighting unit placed in the thoracic cavity or abdominal cavity of the human is provided. Therefore, when the thoracic cavity or abdominal cavity is operated, the interior of the thoracic cavity or abdominal cavity is illuminated, and thus, is less likely to be shadowed, thereby improving the safety of medical treatments.

According to the seventh aspect of the invention, the protector for protecting the wound region is fitted with the auxiliary lighting unit, the auxiliary lighting unit can be fixed to a human in a minimally invasive manner.

According to the eighth aspect of the invention, the auxiliary lighting unit includes the needle. Therefore, the auxiliary lighting unit can be fixed at an optional location in the thoracic cavity or abdominal cavity, thereby reliably illuminating a desired region.

According to the ninth aspect of the invention, the illumination angle of light can be changed. Therefore, the healthcare worker can take a posture facilitating performing medical treatment.

DESCRIPTION OF EMBODIMENTS

Embodiments of the present invention will be described hereinafter in detail with reference to the drawings. The following preferred embodiments are set forth merely for the purposes of examples in nature, and are not intended to limit the scope, applications, and use of the invention.

First Embodiment

Figure 1:
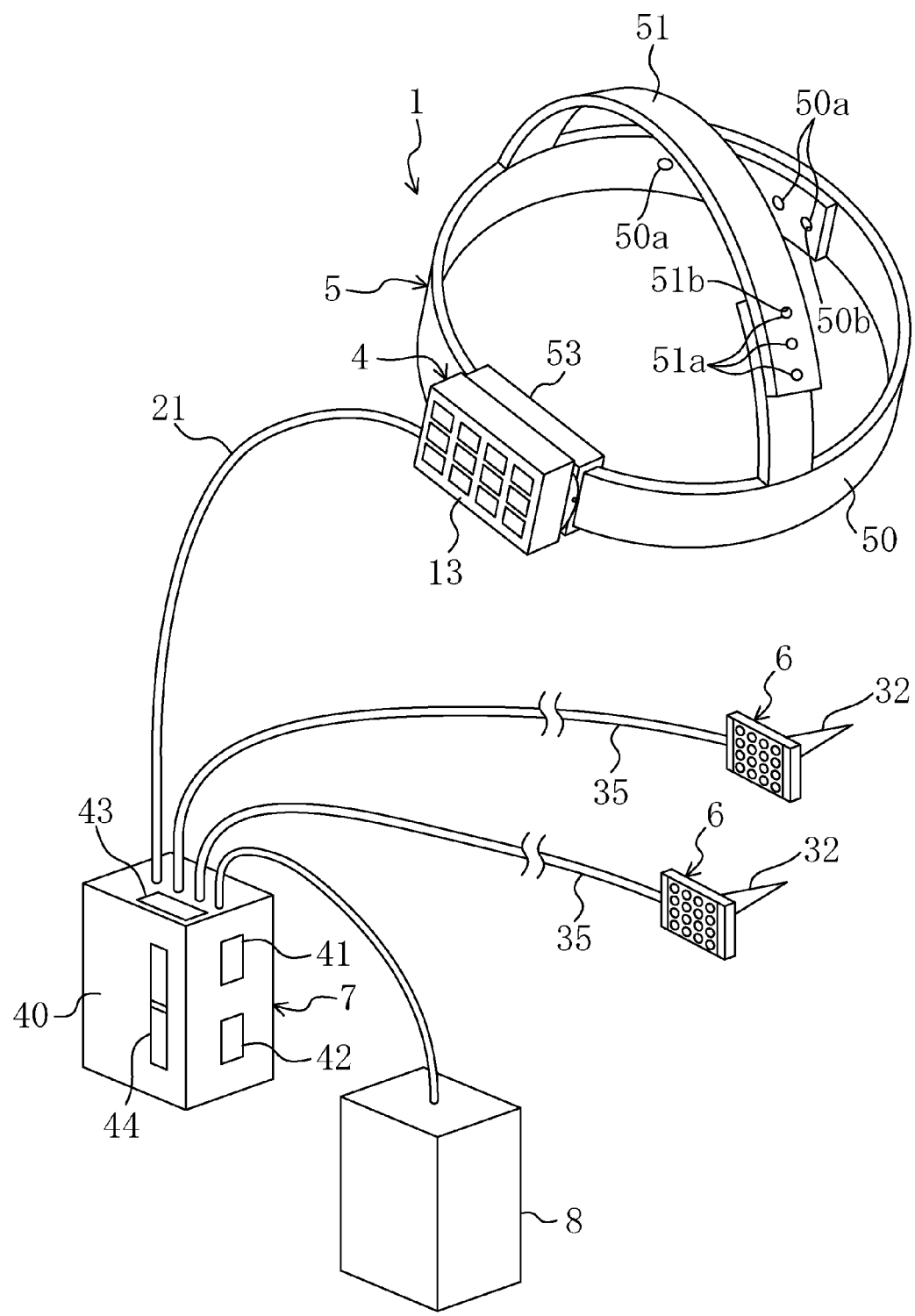
FIG. 1 is a perspective view of a lighting system according to a first embodiment.

FIG. 1 illustrates a lighting system 1 according to a first embodiment of the present invention. The lighting system 1 is for use in surgery in, e.g., a thoracic cavity or an abdominal cavity S of a human (illustrated in FIGS. 5 and 6). The lighting system 1 includes a light emitting unit 4, a securing member 5 for securing the light emitting unit 4 to the head of a doctor A (illustrated in FIG. 4) who is a healthcare worker, two auxiliary lighting units 6, 6, and a power supply 7 for supplying power to the light emitting unit 4 and the auxiliary lighting units 6, 6. The lighting system 1 can be used not only by the doctor A, but also by nurses, etc.

Figure 2:
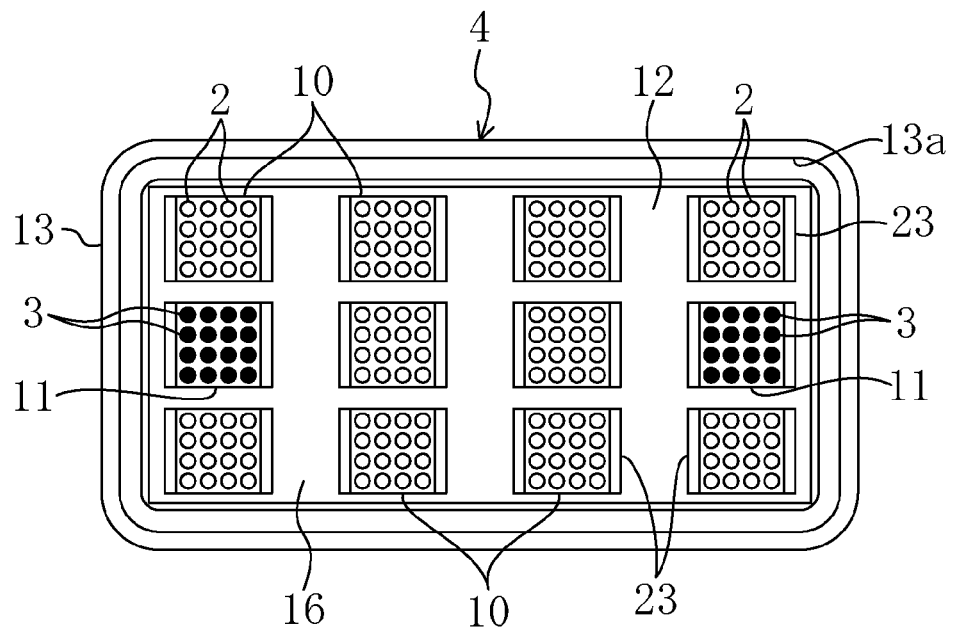
FIG. 2 is a front view of a light emitting unit.
Figure 3:
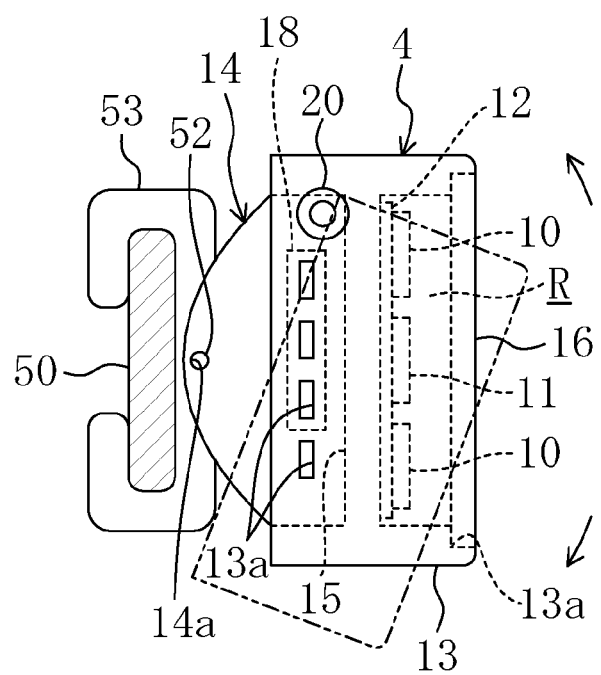
FIG. 3 is a side view of the light emitting unit and a support member.

As illustrated in FIGS. 2 and 3, the light emitting unit 4 includes a plurality of white light emitting diode mounting boards 10, 10, . . . on which white light emitting diodes 2, 2, . . . are mounted, a plurality of red light emitting diode mounting boards 11, 11, . . . on which red light emitting diodes 3, 3, . . . are mounted, an attachment board 12 to which the mounting boards 10 and 11 are detachably attached, and a housing 13 in which the boards 10, 11, and 12 are contained. In FIG. 2, the red light emitting diodes 3 are indicated by filled circles.

The housing 13 forms a rectangular parallelepiped having a larger lateral dimension in a situation (illustrated in FIG. 4) where the doctor A is wearing the housing 13. A material of the housing 13 is, for example, a material with good heat dissipation characteristics, such as an aluminum alloy. An accommodation space R (illustrated only in FIG. 3) in which the boards 10, 11, and 12 are contained is formed in the housing 13. The accommodation space R is open to the front face of the housing 13 so that the opening of the space R forms a generally rectangular shape. A board locking plate 15 onto which the attachment board 12 is locked is provided inside the accommodation space R to extend vertically. Cooling vents (not shown) for cooling the light emitting diodes 2 and 3 generating heat when lighted are formed in the board locking plate 15.

A cooling fan 18 is placed near the back of the board locking plate 15 in the housing 13. Exhaust holes 13a, 13a, . . . are formed in side surfaces of the housing 13 to communicate with a portion of the interior of the housing 13 in which the cooling fan 18 is placed. The exhaust holes 13a each include a filter made of fibers combining repellency and air permeability, such as GORE-TEX®. This reduces the discharge of dust, etc., in the housing 13 to the outside. A material of the filter may be, e.g., a nonwoven fabric.

The cooling fan 18 is of a low-noise type for use in, e.g., a personal computer, and thus, the doctor A is less likely to hear the operating noise. Operation of the cooling fan 18 allows the feed of air to the light emitting diodes 2, 3, etc. The air of which temperature is increased by cooling the light emitting diodes 2, 3, etc., is discharged through the exhaust holes 13a in the lateral directions of the housing 13. Thus, the air the temperature of which is increased is not in direct contact with the doctor A and a patient C.

A material of the housing 13 is not limited to an aluminum alloy, and can be a heat-resistant resin material. A thermoelectric device (not shown), such as a Peltier device, may be provided instead of the cooling fan 18 to cool the light emitting diodes 2, 3, etc.

As illustrated in FIG. 3, a step 13a is formed at the edge of the opening of the accommodation space R in the housing 13. A lens 16 is fitted to the step 13a. The lens 16 is formed in the shape of a rectangular plate to cover the opening of the accommodation space R, and can be made of, e.g., a resin material or glass. Side plates 14 are formed on the (back) face of the housing 13 opposite to the lens 16 to project beyond both longitudinal sides of the housing 13. A through hole 14a through which a spindle 52 of the securing member 5 is inserted is formed to pass through each of the side plates 14 along the longitudinal direction of the housing 13.

Figure 4:
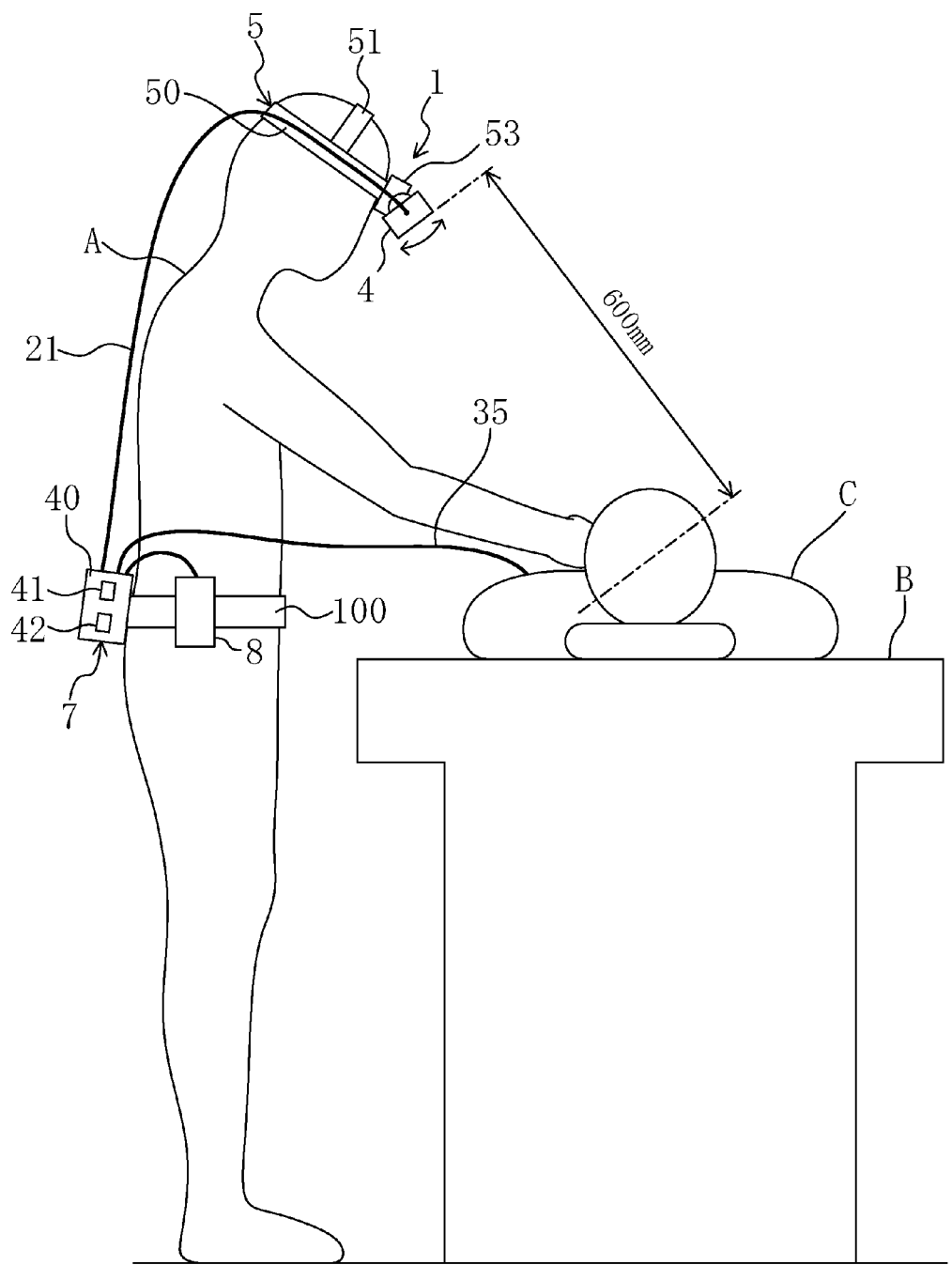
FIG. 4 is a diagram for explaining a situation where the lighting system is used.

A terminal 20 is provided on a side surface of the housing 13. As illustrated in FIGS. 1 and 4, a power cord 21 extending from the power supply 7 is connected to the terminal 20.

The attachment board 12 forms a rectangular shape having a larger lateral dimension. The surface of the attachment board 12 is coated with a reflective material which reflects light. As illustrated in FIG. 2, twelve connectors 23, 23, . . . to which the mounting boards 10 and 11 are detachably attached are provided on the surface of the attachment board 12, and are arranged in a matrix of three columns and four rows. A predetermined gap is provided between each adjacent pair of the connectors 23, 23, . . . . The attachment board 12 includes wires (not shown) electrically connected to terminals (not shown) of the connectors 23. The wires of the attachment board 12 are electrically connected to the terminal 20 of the housing 13.

Figure 7:
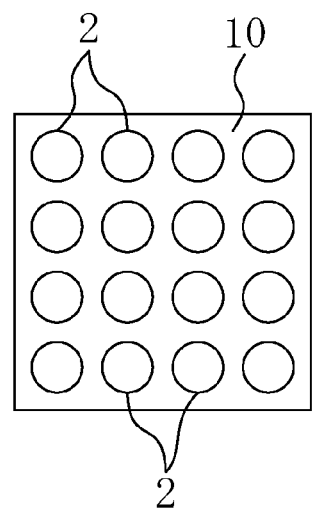
FIG. 7 is a front view of a white light emitting diode mounting board.
Figure 8:
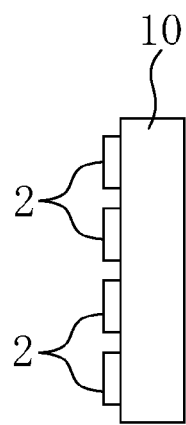
FIG. 8 is a side view of the white light emitting diode mounting board.

The white light emitting diode mounting boards 10 each form, e.g., a 10 mm square. As illustrated in FIGS. 7 and 8, a total of sixteen white light emitting diodes 2, 2, . . . are provided on the surface of each of the white light emitting diode mounting boards 10 so as to be arranged in a matrix of four columns and four rows. A predetermined gap is formed between each adjacent pair of the white light emitting diodes 2, 2, . . . . Terminals (not shown) are provided on the back faces of the white light emitting diode mounting boards 10 so as to be electrically connected to the white light emitting diodes 2. Terminals of the white and red light emitting diode mounting boards 10 and 11 are connected to the terminals of the connectors 23 on the attachment board 12. The configuration of each of the red light emitting diode mounting boards 11 is similar to that of each of the white light emitting diode mounting boards 10.

The dimensions and shape of the white and red light emitting diode mounting boards 10 and 11 are not limited to the above-described dimensions and shape. The number and arrangement of the white light emitting diodes 2 mounted on the single board 10 and the number and arrangement of the red light emitting diodes 3 mounted on the single board 11 are limited to the above-described number and arrangement, and can be optionally set. In order to obtain a sufficient brightness level, the density of the white and red light emitting diodes 2 and 3 is preferably greater than or equal to 25 diodes per square centimeter. The intensities of light beams emitted from the white light emitting diode mounting boards 10, 10, . . . may be different.

Figure 9:
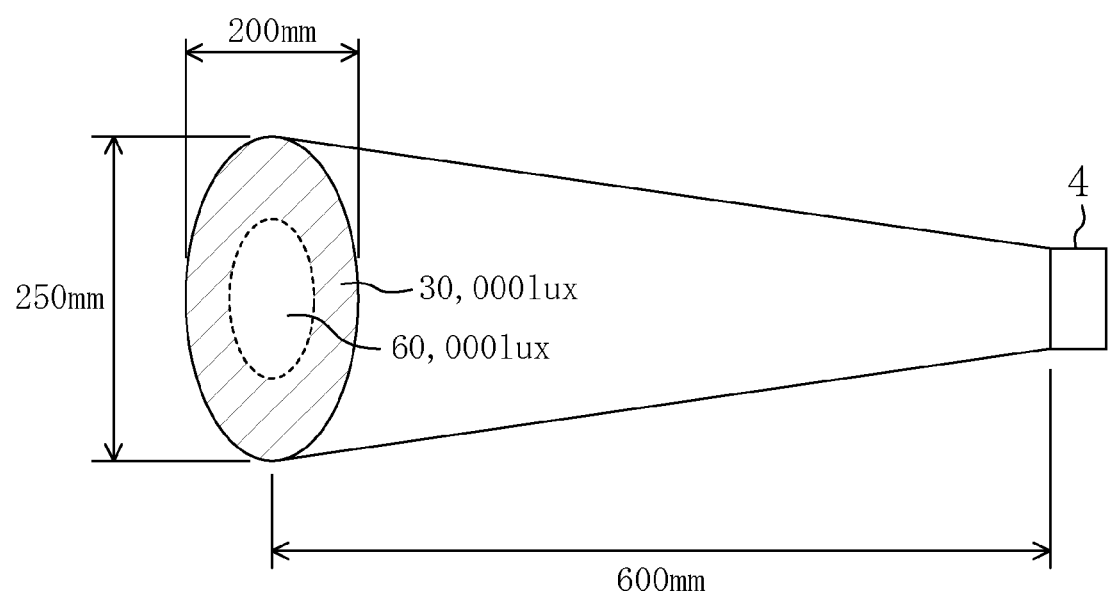
FIG. 9 is a diagram for explaining a range irradiated with light by the light emitting unit and the brightness level of the light.

The intensity of light emitted from the light emitting unit 4 can be changed depending on the number of the light emitting diodes 2 and 3, the number of the mounting boards 10 and 11, the types of the light emitting diodes 2 and 3, a supply voltage, etc. The range irradiated with light can be optionally set based on the design of the lens 16 and the location at which the light emitting diodes 2 and 3 are placed. In this embodiment, as illustrated in FIG. 9, at a location spaced 600 mm apart from the front face of the light emitting unit 4 in a direction orthogonal to the front face, the illuminance of the interior of a substantial ellipse the length of the major axis of which is 250 mm and the length of the minor axis of which is 200 mm is set at 30,000-60,000 lux. Specifically, as illustrated in FIG. 9, a central region of the ellipse surrounded by the broken line has an illuminance of 60,000 lux. The broken line forms a substantial ellipse the length of the major axis of which is approximately 150 mm and the length of the minor axis of which is approximately 100 mm. A shaded region of the ellipse except the region thereof surrounded by the broken line has an illuminance of at least 30,000 lux. The illuminance of the region surrounded by the broken line is preferably greater than or equal to 40,000 lux.

Figure 5:
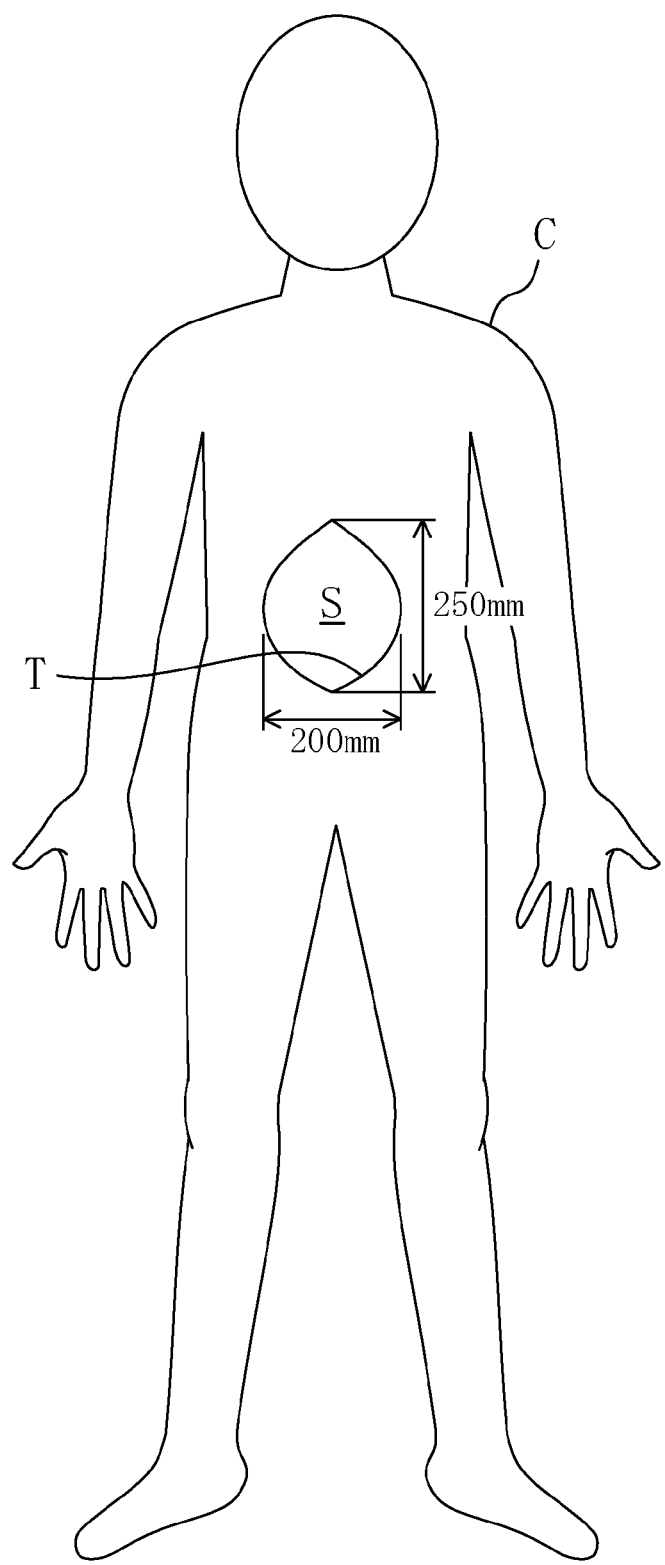
FIG. 5 is a diagram illustrating a patient who undergoes surgery with the use of the lighting system.
Figure 6:
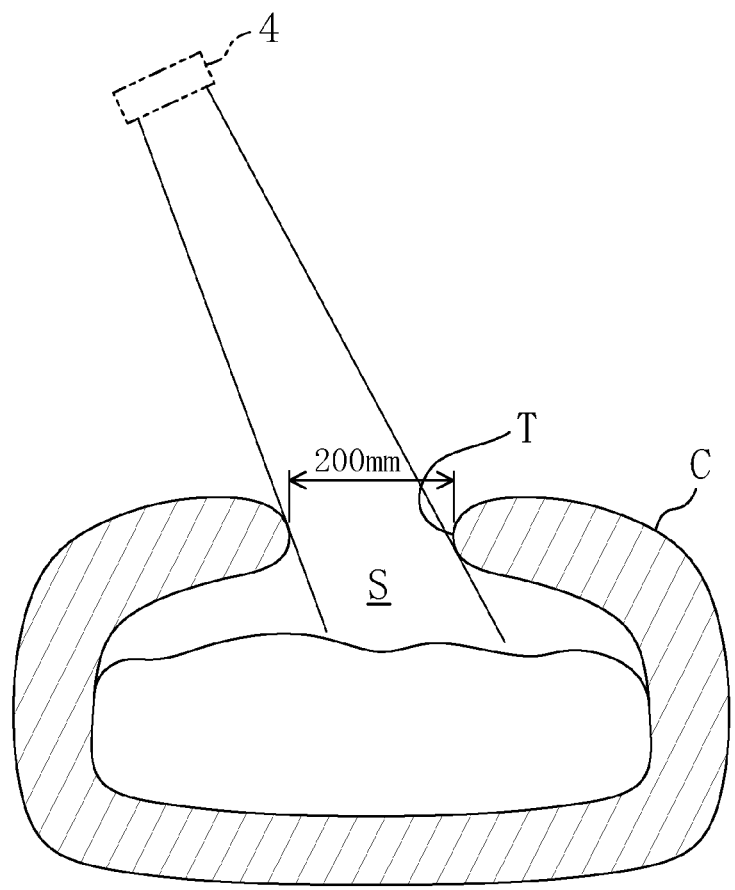
FIG. 6 is a cross-sectional view of an abdominal cavity of the patient.

The substantial ellipse the length of the major axis of which is 250 mm and the length of the minor axis of which is 200 mm is a shape corresponding to the shape of an incision site T formed when the chest or abdomen of the patient C illustrated in FIGS. 5 and 6 is operated. Thus, when the illuminance of the range forming the substantial ellipse is 30,000-60,000 lux, such an illuminance can accommodate most of surgical operations of the chest and abdomen.

When the illuminance is set as described above, this enables illumination of a wide region of a surgical field at a sufficient brightness level without a shadowless lamp during surgery, and does not interfere with a procedure. When the illuminance is too high, the white light emitting diodes 2 or the red light emitting diodes 3 are disconnected from the corresponding connectors 23, thereby enabling the adjustment of the illuminance. The focus of light and the range irradiated with light can be changed depending on the design of the lens 16. Regions of the range irradiated with light can be irradiated with light at different intensities depending on the design of the lens 16.

Figure 10:
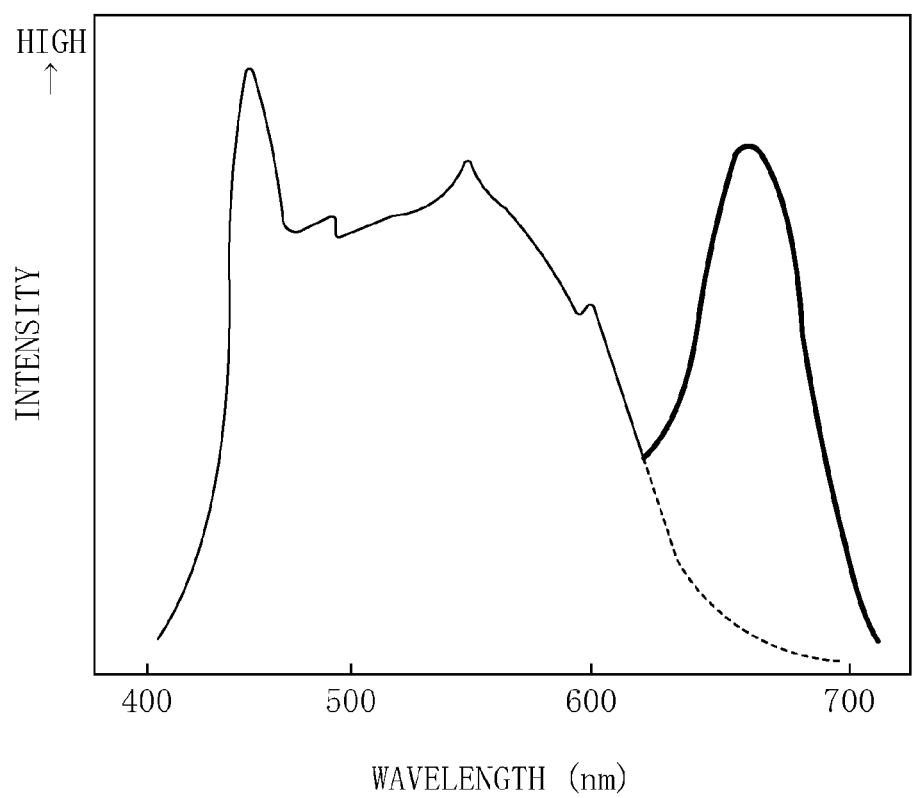
FIG. 10 is a graph illustrating the spectrum of light from the light emitting unit.

The color reproducibility and color rendering can be changed depending on the ratio between the number of the white light emitting diodes 2 of the light emitting unit 4 and the number of the red light emitting diodes 3 thereof. In this embodiment, when human tissue is irradiated with light from the light emitting unit 4, the color reproducibility and color rendering are set suitable for observing the human tissue. As illustrated by the emission spectrum in FIG. 10, when the light emitting unit 4 includes only the white light emitting diodes 2 (as illustrated by the broken line), the light intensity in a red region having a wavelength greater than or equal to 600 nm is significantly low, and thus, light emitted by the light emitting unit 4 is not so suitable as light for surgery because the light is less likely to clearly show a red color, such as the color of blood, in observation of human tissue, in particular, incised tissue. However, when the red light emitting diodes 3 are provided (as illustrated by the bold solid line), the light intensity in the red region increases, thereby obtaining the color reproducibility and color rendering suitable for observing human tissue. When the light intensity in the red region is to be changed, the white light emitting diode mounting boards 10 are disconnected from the corresponding connectors 23, and red light emitting diode mounting boards 11 are attached to the connectors 23, thereby increasing the light intensity in the red region. Specifically, in this embodiment, the color reproducibility and color rendering can be easily changed by attachment and removal of the mounting boards 10 and 11, thereby changing the color reproducibility and color rendering depending on the patient C and changing the color reproducibility and color rendering depending on the preferences of the doctor A.

Each of the white light emitting diode mounting boards 10 may include different types of the white light emitting diodes 2.

Although not shown, instead of white light emitting diodes 2 and red light emitting diodes 3, mounting boards on which, e.g., light emitting diodes emitting infrared rays are mounted may be attached to some of the connectors 23. In this case, the infrared rays are preferably near infrared rays each having a wavelength of 900-1100 nm. Color balance can be also modified by changing the ratio between the number of the white light emitting diodes 2 and the number of the red light emitting diodes 3.

A heat insulator is preferably provided on the back of the housing 13. The provision of the heat insulator makes it difficult to transfer heat from the light emitting diodes 2 and 3 to the doctor A, thereby improving usability.

Figure 11:
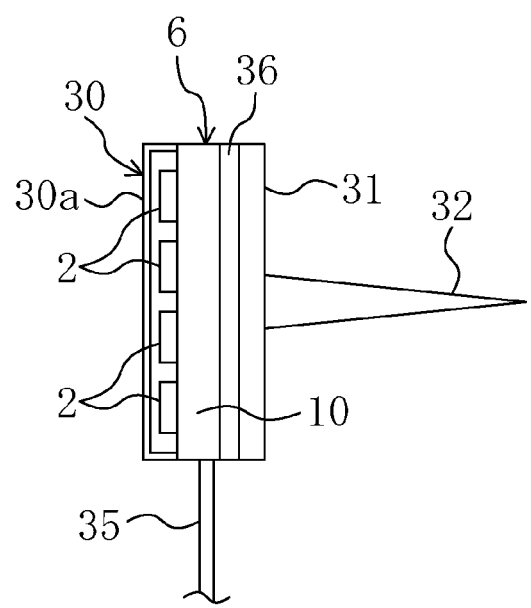
FIG. 11 is a side view of an auxiliary lighting unit.

As illustrated in FIG. 11, the auxiliary lighting units 6 each include a white light emitting diode mounting board 10 on which white light emitting diodes 2 are mounted, a front cover 30 and a back cover 31 covering the front face and the back face, respectively of the mounting board 10, a heat insulator 36, and a fixing needle 32. The configuration of the white light emitting diode mounting board 10 is similar to that of each of the above-described white light emitting diode mounting boards 10. A portion of the front cover 30 opposed to the light emitting diodes 2 includes a lens 30a. A power cord 35 extending to the power supply 7 is connected to a wire for the white light emitting diode mounting board 10. Although not shown, a distal end portion of the power cord 35 includes a terminal connected to the terminal of the power supply 7. When the auxiliary lighting unit 6 is not used, the terminal of the power cord 35 can be removed from the terminal of the power supply 7.

The heat insulator 36 is provided between the white light emitting diode mounting board 10 and the back cover 31, and is configured to reduce transfer of heat generated by the white light emitting diodes 2 to the back cover 31 and the needle 32. The heat insulator 36 can be made of various foamed materials, etc. The thermal insulation performance of the heat insulator 36 is set so that even when the white light emitting diodes 2 are lighted continuously for a few hours, the temperatures of the back cover 31 and the needle 32 do not exceed 38° C. This prevents low temperature burns.

The needle 32 is provided to project backward from the back cover 31. The auxiliary lighting unit 6 can be fixed at an optional location by inserting the needle 32 into human tissue. The needle 32 is preferably made of a material hardly having an adverse effect on a living body, and is preferably made of, e.g., stainless steel or a titanium alloy. The auxiliary lighting unit 6 may include a red light emitting diode and/or a light emitting diode emitting an infrared ray.

As illustrated in FIG. 1, the power supply 7 includes a battery case 40 in which one or more batteries are contained. The battery case 40 includes a switch 41 for lighting the light emitting unit 4, and a switch 42 for lighting the auxiliary lighting units 6, and the light emitting unit 4 and the auxiliary lighting units 6 can be individually lighted. The battery case 40 also includes a display 43 for displaying the remaining battery charge, and a brightness control switch 44. The intensity of light emitted from the light emitting diodes 2 and 3 can be adjusted by operating the brightness control switch 44. The reference character 8 illustrated in FIG. 1 denotes a standby battery, and when the battery in the power supply 7 has been exhausted, power is supplied from the standby battery 8. The power supply 7 may include an adjuster for adjusting the intensity of light emitted from the light emitting unit 4.

As illustrated in FIG. 4, the power supply 7 and the standby battery 8 can be fixed to the waist of the doctor A using, e.g., a belt 100. A chargeable battery may be contained in the power supply 7, and in this case, the chargeable battery is preferably a LiH battery. Multiple ones of the standby battery 8 are preferably prepared. When a battery is used as the power supply, this provides an advantage that electromagnetic interference with peripheral medical devices is less likely to be caused.

The capacities of the power supply 7 and the standby battery 8 are set so that the time period during which the light emitting unit 4 is lighted can be approximately 4-5 hours.

As illustrated in FIG. 1, the securing member 5 includes a head band 50 extending around the head, a support band 51 extending through the top of the head, and a support member 53 for supporting the light emitting unit 4. Both longitudinal end portions of the head band 50 are formed to overlap with each other in the thickness direction at the back of the head. One longitudinal end portion of the head band 50 includes a plurality of holes 50a, 50a, . . . spaced in the longitudinal direction, and the other longitudinal end portion thereof includes a protrusion 50b configured so as to be inserted into any one of the holes 50a. The insertion of the protrusion 50b into any one of the holes 50a allows the head band 50 to form a circular shape. In this case, the diameter of the head band 50 can be changed depending on the hole 50a into which the protrusion 50b is inserted. The use of another structure may allow change of the diameter of the head band 50.

The support band 51 is connected integrally to the head band 50, and a longitudinal middle portion of the support band 51 is cut, thereby allowing the separated portions of the support band 51 to overlap with each other in the thickness direction. Similar to the head band 50, one of the portions of the support band 51 overlapping with each other in the thickness direction includes holes 51a, and the other portion includes a protrusion 51b, thereby adjusting the length of the support band 51.

As illustrated in FIG. 3, the support member 53 is formed to engage the head band 50. The support member 53 includes a spindle 52 extending along the lateral direction of a wearer. The spindle 52 is inserted through the through holes 14a of the side plates 14 of the housing 13. While the spindle 52 is inserted through the through holes 14a, the light emitting unit 4 is supported by the securing member 5, and furthermore, the light emitting unit 4 rotates vertically (in the directions illustrated by the arrows in FIGS. 3 and 4) about the spindle 52, thereby adjusting the angle of the light emitting unit 4, i.e., changing the illumination angle of light. The spindle 52 and the through holes 14a form an illumination angle changer of the present invention.

Although not shown, the light emitting unit 4 includes a screw for fixing the light emitting unit 4 to the support member 53 when the light emitting unit 4 has rotated to a desired rotation angle. However, the screw may be omitted, and a resistance may be imparted to the light emitting unit 4 to prevent the light emitting unit 4 from unintentionally rotating. The range in which the light emitting unit 4 rotates is preferably about 10°-90°. A structure for adjusting the angle of the light emitting unit 4 is not limited to the above-described structure, and various structures can be used.

Next, a case in which the lighting system 1 configured as described above is used will be described. The reference character B in FIG. 4 denotes an operating table.

First, the diameter of the head band 50 and the length of the support band 51 are adjusted to correspond to the head of the doctor A who is a healthcare worker, and the light emitting unit 4 is fixed to the head of the doctor A. In this case, the light emitting unit 4 is located on the forehead of the doctor A, and furthermore, the angle of the light emitting unit 4 is adjusted. The power supply 7 and the standby battery 8 are worn with the belt 100 by the doctor A. When the light emitting diodes 2 and 3 of the light emitting unit 4 are lighted by operating the switch 41, and then the doctor A turns his or her face to a surgical field, the light emitting unit 4 moves with the movement of the doctor A, thereby illuminating the surgical field with the light emitting unit 4. In this case, even when a region irradiated with light is 600 mm apart from the front face of the light emitting unit 4, the illuminance of the region is 30,000-60,000 lux, thereby providing a sufficient brightness level for performing surgery even without a shadowless lamp. Such a wide range is brightly illuminated, and thus, when sudden bleeding from a region other than a region undergoing a procedure has been caused, the doctor A can recognize the bleeding.

Depending on the build of the patient C, the subcutaneous fat layer and the muscle layer may be thick, and the thoracic cavity or abdominal cavity may be deep (approximately 200-500 mm deep). Even in this case, since the illuminance of the region which is 600 mm apart from the light emitting unit 4 is kept at 60,000 lux, a deep portion of the thoracic cavity or the abdominal cavity S can be illuminated at an illuminance greater than or equal to 30,000 lux, thereby preventing a procedure from being interfered with.

In illumination of a surgical field, the light emitting unit 4 is fixed to the head of the doctor A, and thus, moves with the movement of the doctor A, and furthermore, the direction of light radiation can be changed as desired by the doctor A by moving his or her head. Furthermore, since the light emitting unit 4 moves only with the movement of the doctor A, dust, etc., is much less likely to fall to the patient C.

Figure 12:
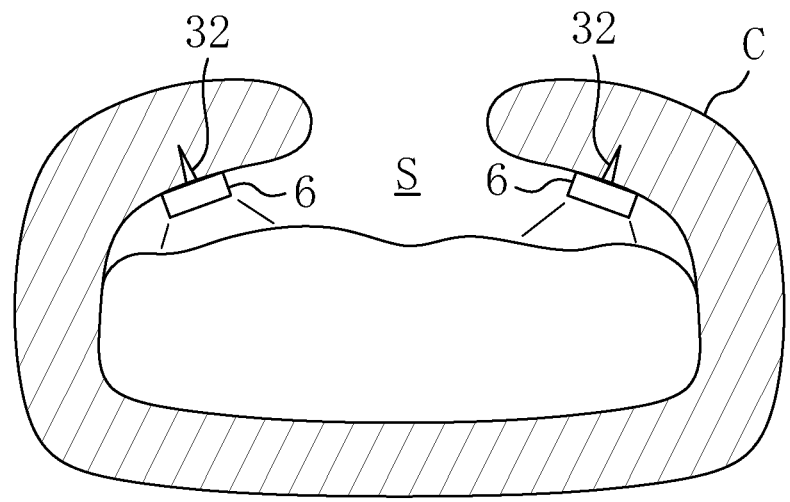
FIG. 12 is a diagram corresponding to FIG. 6 and illustrating a situation where the auxiliary lighting unit is used.

After incision of body surface tissue, the auxiliary lighting units 6 are placed in the thoracic cavity or the abdominal cavity S as illustrated in FIG. 12. Specifically, the needle 32 of each of the auxiliary lighting units 6 is inserted from the inside into tissue in the vicinity of a wound region formed by the incision, thereby fixing the auxiliary lighting unit 6 to the patient C. When the light emitting diodes 2 of the auxiliary lighting unit 6 are lighted by operating the switch 42 of the power supply 7, the interior of the thoracic cavity or the abdominal cavity S is directly illuminated. Thus, the interior of the thoracic cavity or the abdominal cavity S is less likely to be shadowed, thereby allowing the doctor A to observe a wider range.

When the patient C is, for example, obese, and the thoracic cavity or the abdominal cavity S is deep, the intensity of light emitted from the light emitting diodes 2 and 3 may be increased by operating the brightness control switch 44, and thus, the light illuminance on a back portion of the thoracic cavity or the abdominal cavity S may be 40,000-60,000 lux.

As described above, the lighting system 1 according to the first embodiment can reliably illuminate the patient C from a location close to the patient C without using a large-scale lighting system, such as a shadowless lamp, during surgery. This eliminates the need for, e.g., reinforcing the ceiling, can reduce the cooling cost and power consumption, and furthermore, eliminates the need for cleaning and sterilization of a shadowless lamp, thereby allowing the cost of introducing the lighting system 1 to be low. Since a lamp unit and a movable mechanism are not required, bacteria-laden dust, etc., is much less likely to fall to the patient C, thereby preventing an infection from being acquired. Since the light emitting unit 4 moves with the movement of the doctor A, the direction of light radiation can be changed as desired by the doctor A, thereby preventing the doctor A from feeling stress during medical treatment.

Since the lighting system 1 can reliably illuminate a necessary region from a location close to the region, medical treatment can be performed in an outpatient treatment room, a cardiac catheterization room, an emergency room, etc., without a shadowless lamp.

The light emitting unit 4 includes the white light emitting diodes 2 and the red light emitting diodes 3, and thus, when illuminating human tissue with the light emitting unit 4, the color reproducibility and color rendering can be set suitable for observing human tissue. This enables blood vessels, etc., to be accurately recognized, thereby improving the safety of medical treatment. Since the light emitting unit 4 includes the red light emitting diodes 3, this reduces glare from light reflected off, e.g., a surgical instrument, and thus, reduces the strain on the eyes of the doctor A, resulting in a reduction in fatigue.

When light emitting diodes emitting infrared rays are provided, the temperature distribution of tissue can be obtained as an image by using an infrared thermography camera. The locations and shapes of blood vessels, the amount of blood flowing through blood vessels, etc., are recognized based on the obtained temperature distribution image, thereby helping medical treatment.

Since the light emitting diodes 2 and 3 are attachable and detachable, the color reproducibility, the color rendering, or the brightness level can be changed.

The auxiliary lighting units 6 placed in the thoracic cavity or the abdominal cavity S of a human are provided, and thus, when the thoracic cavity or the abdominal cavity S is operated, the interior of the thoracic cavity or the abdominal cavity S is illuminated, and thus, is less likely to be shadowed, thereby improving the safety of medical treatment.

Since the auxiliary lighting units 6 each include the needle 32, the auxiliary lighting units 6 can be fixed to an optional location in the thoracic cavity or the abdominal cavity S, thereby reliably illuminating a desired region.

Since the angle of the light emitting unit 4 can be adjusted, the doctor A can take a posture facilitating performing surgery.

The light emitting unit 4 may include either or both of green light emitting diodes and blue light emitting diodes other than the white light emitting diodes 2 and the red light emitting diodes 3. Also when green light emitting diodes and/or blue light emitting diodes are provided, mounting boards on which the light emitting diodes are mounted can be connected to corresponding connectors 23. Provision of green light emitting diodes and/or blue light emitting diodes allows the spectrum of light emitted from the light emitting unit 4 to be closer to the spectrum of natural light, and thus, fatigue is reduced by reducing the strain on the eyes of the doctor A. The auxiliary lighting units 6 may each include green light emitting diodes and/or blue light emitting diodes.

In the above-described embodiment, a case in which the lighting system 1 includes two auxiliary lighting units 6, 6, was described. However, the number of the auxiliary lighting units 6 is not limited, and the number of the auxiliary lighting units 6 may be one or be greater than or equal to three. Alternatively, the auxiliary lighting units 6 may be omitted.

Figure 13:
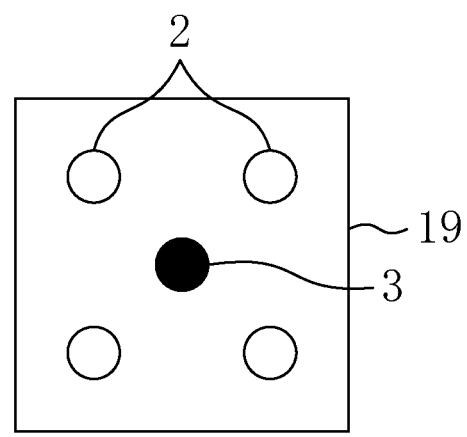
FIG. 13 is a diagram corresponding to FIG. 7 according to a first variation of the first embodiment.

As in a first variation illustrated in FIG. 13, white light emitting diodes 2 and a red light emitting diode 3 may be mounted on a single mounting board 19. In the first variation, the four white light emitting diodes 2 are placed on an outer portion of the mounting board 19, and the red light emitting diode 3 is placed on a central portion of the mounting board 19. The number of white light emitting diodes 2 and the number of red light emitting diodes 3 can be optionally set.

Figure 14:
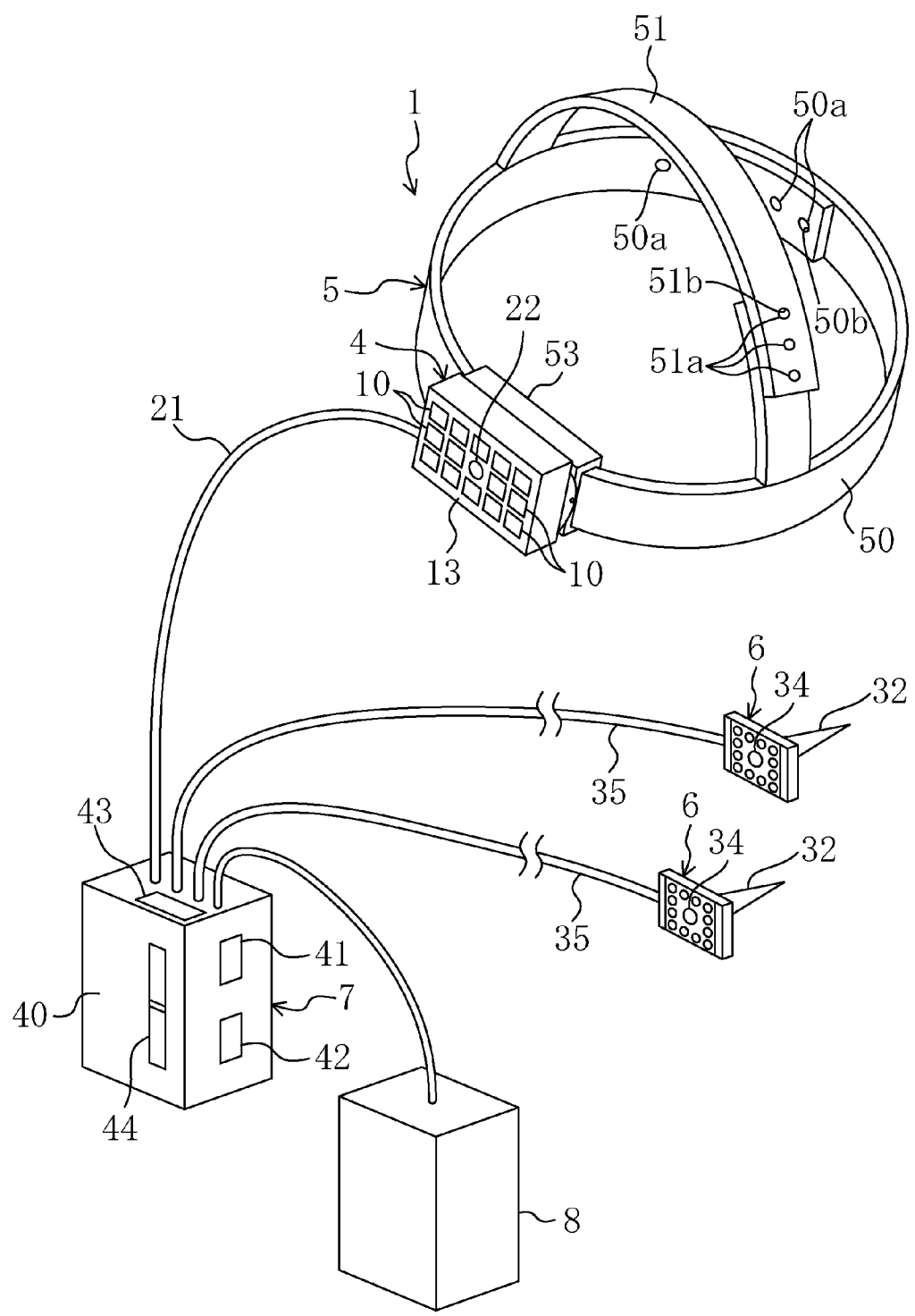
FIG. 14 is a diagram corresponding to FIG. 1 according to a second variation of the first embodiment.
Figure 15:
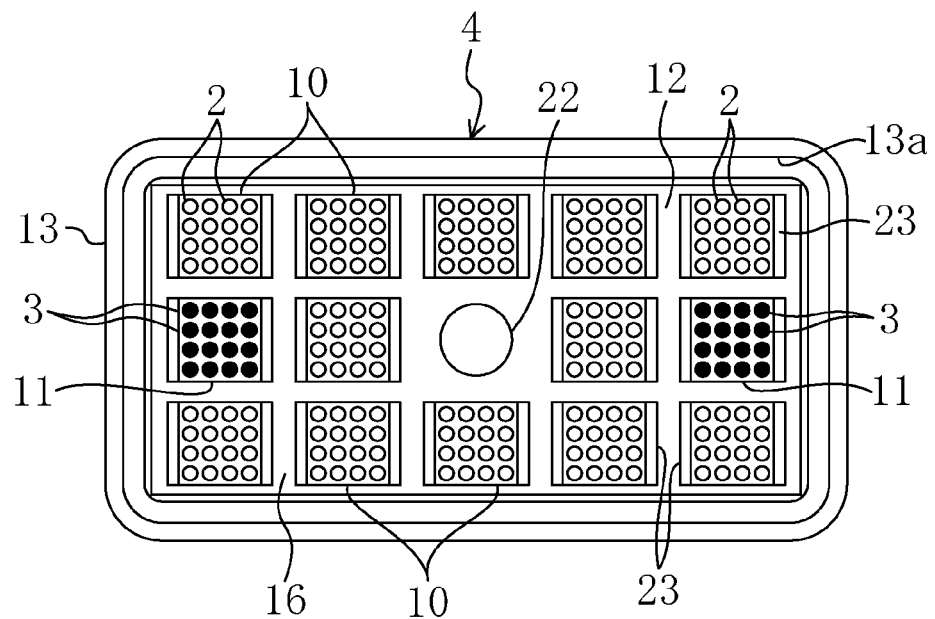
FIG. 15 is a diagram corresponding to FIG. 2 according to the second variation of the first embodiment.
Figure 16:
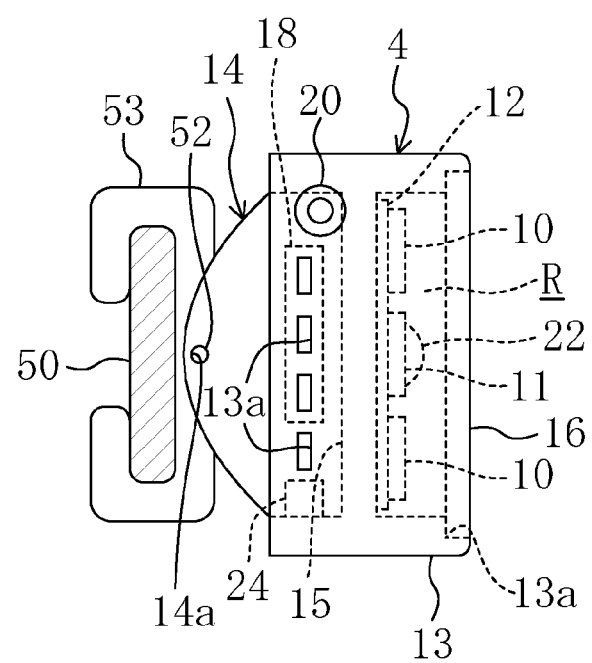
FIG. 16 is a diagram corresponding to FIG. 3 according to the second variation of the first embodiment.

As in a second variation illustrated in FIGS. 14-16, the light emitting unit 4 may include a camera 22. The camera 22 is an infrared camera. A radio transmitter 24 (illustrated in FIG. 16) is provided in the housing 13 of the light emitting unit 4 to transmit, by radio, a picture taken by the camera 22. The picture transmitted by radio is displayed on a monitor (not shown) placed in an operating room. The doctor A can check the picture on the monitor.

Alternatively, the auxiliary lighting units 6 may each include such a camera. Thus, a less visible region of the interior of the thoracic cavity or the abdominal cavity S can be checked on the monitor. In this second variation, the auxiliary lighting units 6 each include a normal camera 34, and a picture taken by the camera 34 is transmitted to the monitor by a radio transmitter which is not shown. This allows the doctor A to check a deep portion of a body cavity on the monitor. Pictures of the cameras 22 and 34 may be transmitted to the monitor through signal lines.

Alternatively, during surgery, a dye, such as indocyanine green (ICG), may be injected into blood of the patient C, and the patient C may be irradiated with infrared rays by infrared light emitting diodes, thereby also conducting surgery while checking the state of blood flow.

Alternatively, the lens 16 can be colored. When the lens 16 is colored orange or red, this enables irradiation of light having a wavelength suitable for observing human tissue, etc., without using the red light emitting diodes 3, thereby facilitating seeing blood vessels, tissue, blood, etc. In this case, the lens 16 itself may be colored, and alternatively, a colored film may be attached to the lens 16. When the film is attached to the lens 16, this can reduce heat dissipation.

Second Embodiment

Figure 17:
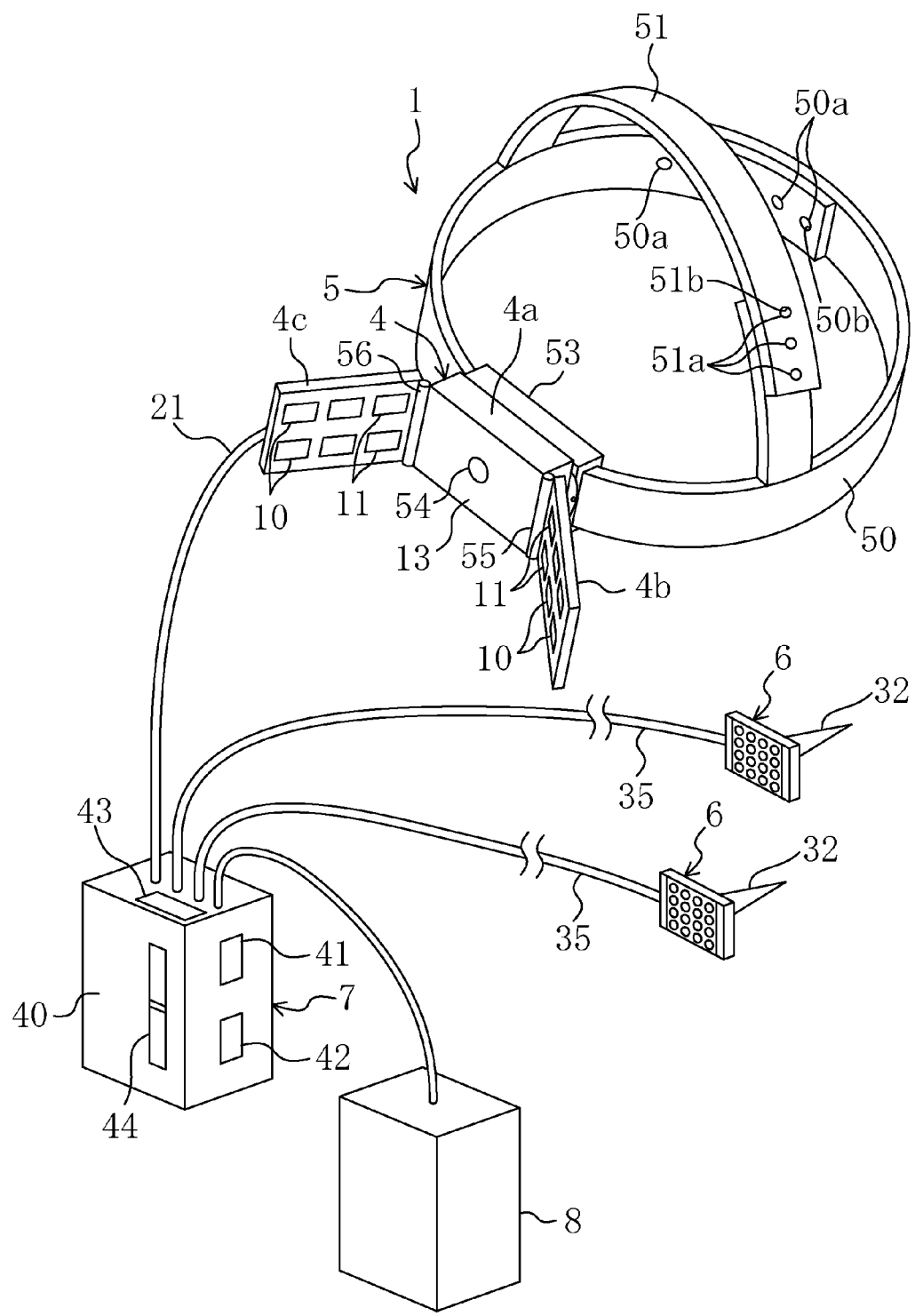
FIG. 17 is a diagram corresponding to FIG. 1 according to a second embodiment.
Figure 18:
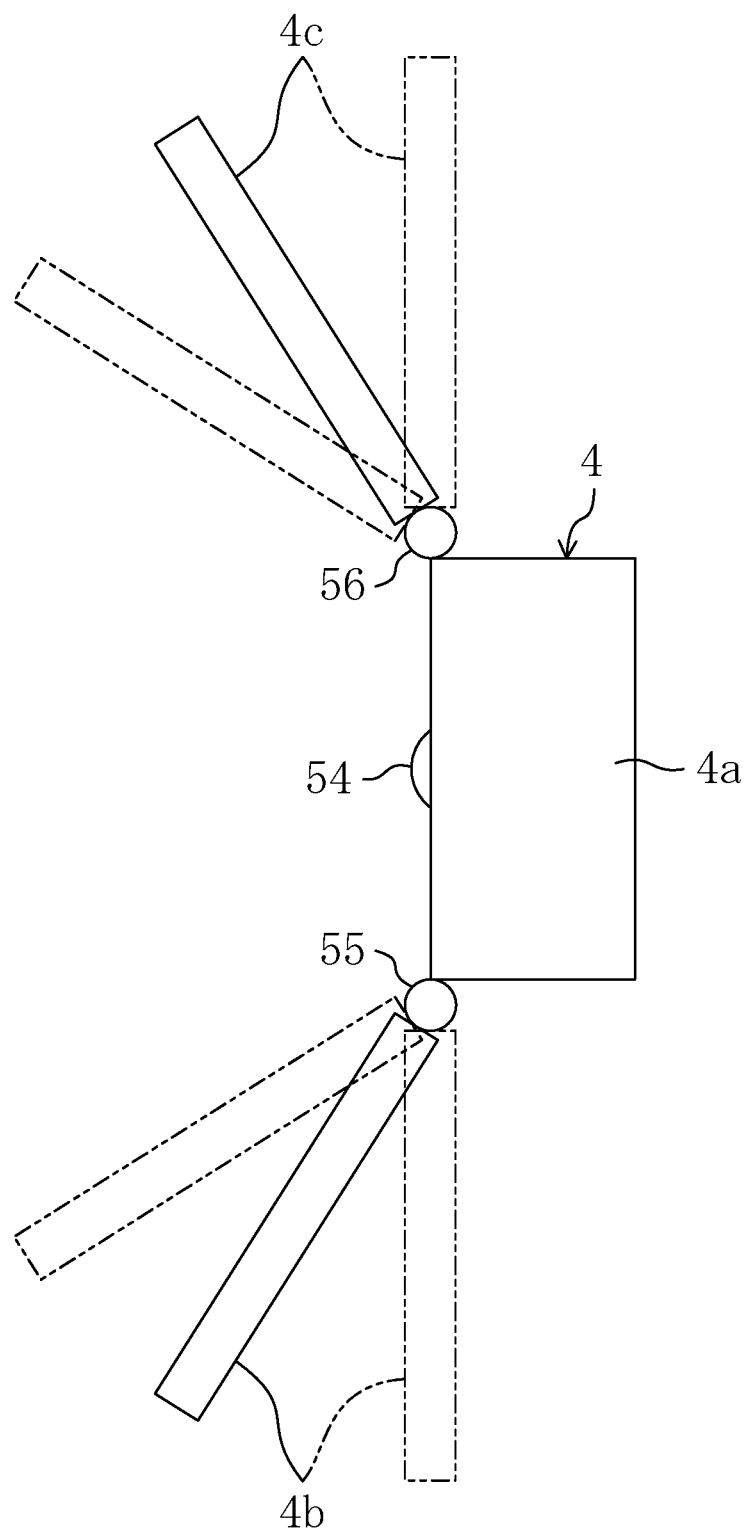
FIG. 18 is a plan view of a light emitting unit according to the second embodiment.

FIGS. 17 and 18 illustrate a lighting system 1 according to a second embodiment of the present invention. Unlike the lighting system 1 of the first embodiment, in the lighting system 1 of the second embodiment, a light emitting unit 4 includes a camera 54, and light emitting diodes 2 and 3 are movably provided in both lateral directions of the camera 54. The other configuration of the second embodiment is identical with that of the first embodiment. In the following description, like reference characters are used to designate elements identical with those of the first embodiment, and description of the elements is omitted. Elements different from those of the first embodiment will be described in detail.

The light emitting unit 4 includes a main body 4a, and left and right light emitting diode attachment members 4b and 4c provided to both the left and right, respectively, of the main body 4a (to both the left and right of a wearer). The main body 4a includes the camera 54. The camera 54 is an infrared camera. Such a radio transmitter (not shown) as in the second variation of the first embodiment is incorporated into the main body 4a.

A hinge mechanism 55 having a rotation axis extending vertically is provided to the left of the main body 4a, and the main body 4a and the left light emitting diode attachment member 4b are coupled together through the hinge mechanism 55. Furthermore, a hinge mechanism 56 similar to the left hinge mechanism is provided to the right of the main body 4a, and the main body 4a and the right light emitting diode attachment member 4c are coupled together through the hinge mechanism 56. Therefore, as illustrated in FIG. 18, the left light emitting diode attachment member 4b rotates about the rotation axis of the hinge mechanism 55, and the right light emitting diode attachment member 4c rotates about the rotation axis of the hinge mechanism 56. When the left and right light emitting diode attachment members 4b and 4c have been rotated to an optional location, the hinge mechanisms 55 and 56 are locked to prevent the attachment members 4b and 4c from unintentionally moving.

The left light emitting diode attachment member 4b is formed in a plate-like shape, and the plurality of white light emitting diode mounting boards 10 and the plurality of red light emitting diode mounting boards 11 of the first embodiment are attached to the front face of the left light emitting diode attachment member 4b. The right light emitting diode attachment member 4c is configured similarly to the left light emitting diode attachment member 4b.

In the second embodiment, the locations of the left light emitting diode attachment member 4b and the right light emitting diode attachment member 4c can be separately adjusted. For example, when the left light emitting diode attachment member 4b and the right light emitting diode attachment member 4c are positioned closer to each other, light beams emitting from both of the attachment members 4c and 4b are localized in a small range, thereby locally illuminating the range. When the left light emitting diode attachment member 4b and the right light emitting diode attachment member 4c are positioned further from each other, a wide range can be illuminated. Specifically, the movement of the left light emitting diode attachment member 4b and the right light emitting diode attachment member 4c enables control of the brightness depending on the depth, etc., of the body cavity of the patient C. The hinge mechanisms 55 and 56 each form an illumination angle changer of the present invention.

Therefore, according to the second embodiment, similar to the first embodiment, a necessary region can be illuminated at low cost without using a large-scale lighting system, such as a shadowless lamp, during surgery, and furthermore, the direction of light radiation can be changed as desired by the doctor A without causing dust, etc., to fall to the patient.

In the second embodiment, the light emitting diodes 2 and 3 can be scattered over a wide range, and thus, heat generated by the light emitting diodes 2 and 3 is less likely to be confined, thereby reducing thermal problems.

Since the left light emitting diode attachment member 4b and the right light emitting diode attachment member 4c are apart from each other, this improves heat dissipation.

The main body 4a may include light emitting diodes 2 and 3. The left and right light emitting diode attachment members 4b and 4c may include the camera 54.

Figure 19:
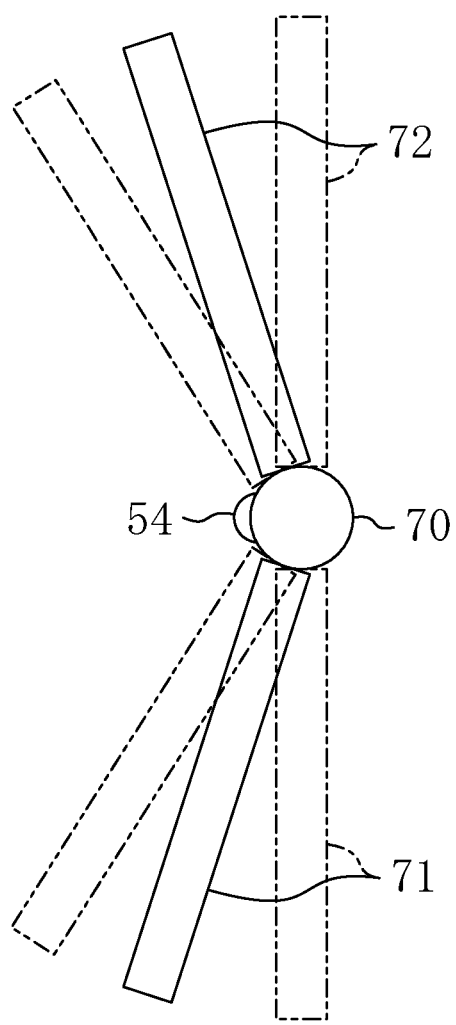
FIG. 19 is a diagram corresponding to FIG. 18 according to a variation of the second embodiment.

As in a variation illustrated in FIG. 19, a left light emitting diode attachment member 71 and a right light emitting diode attachment member 72 may be connected together through a single hinge mechanism 70. Boards, etc., for control are incorporated into the left light emitting diode attachment member 71 and the right light emitting diode attachment member 72. This can reduce the size of the lighting system 1. The hinge mechanism 70 is fitted with the camera 54.

The left light emitting diode attachment member 4b or 71 and the right light emitting diode attachment member 4c or 72 may be moved by utilizing an electric actuator, such as a motor. In this case, the power supply 7 can include switches for moving the left light emitting diode attachment member 4b or 71 and the right light emitting diode attachment member 4c or 72.

Third Embodiment

Figure 20:
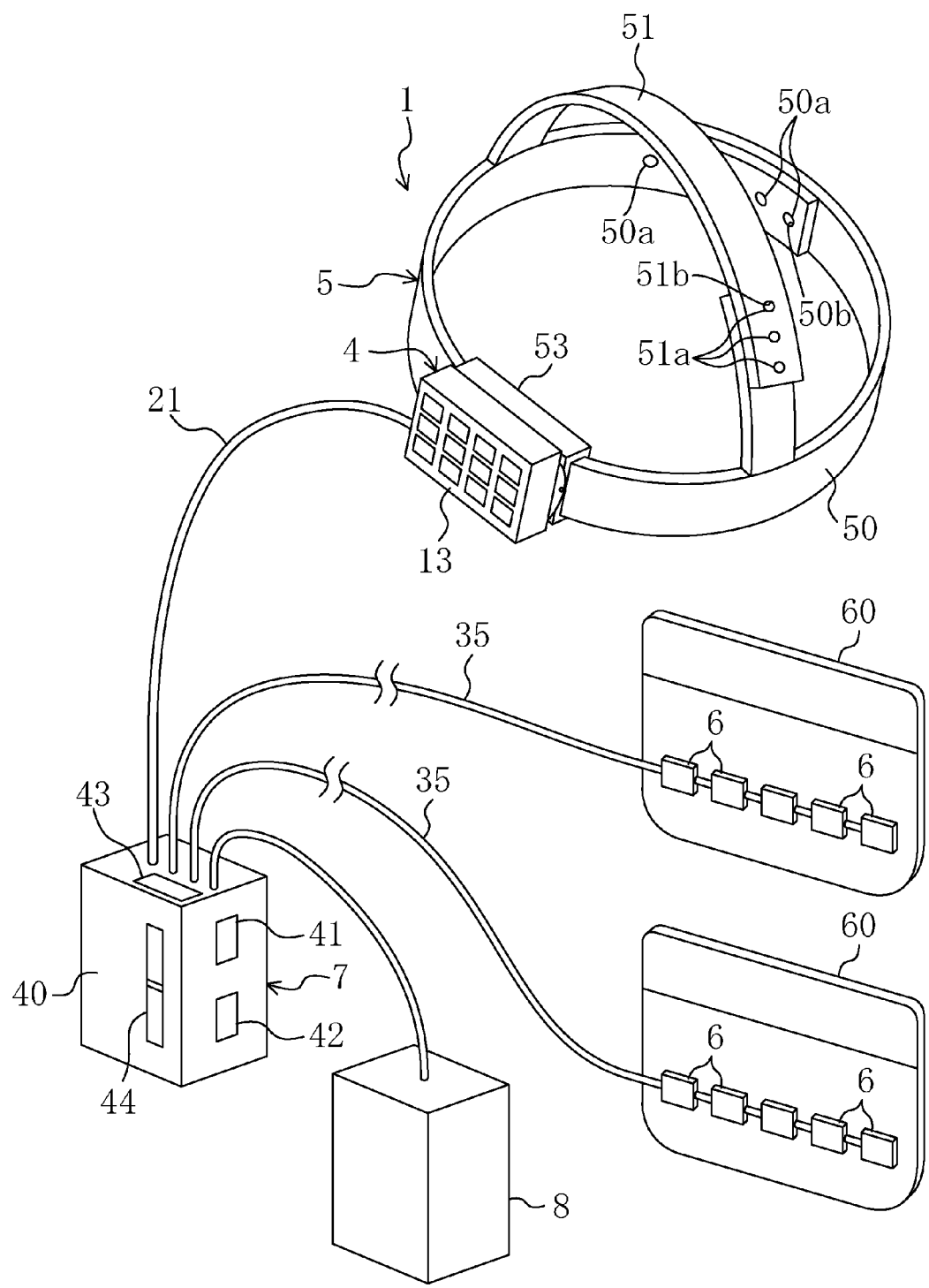
FIG. 20 is a diagram corresponding to FIG. 1 according to a third embodiment.

FIG. 20 illustrates a lighting system 1 according to a third embodiment of the present invention. Unlike the lighting system 1 of the first embodiment, in the lighting system 1 of the third embodiment, auxiliary lighting units 6 are fixed to a patient C (illustrated in FIGS. 23 and 24) by using protectors 60 (see FIG. 21) for protecting a wound region of the patient C. The other configuration of the third embodiment is identical with that of the first embodiment. In the following description, like reference characters are used to designate elements identical with those of the first embodiment, and description of the elements is omitted. Elements different from those of the first embodiment will be described in detail.

Figure 22:
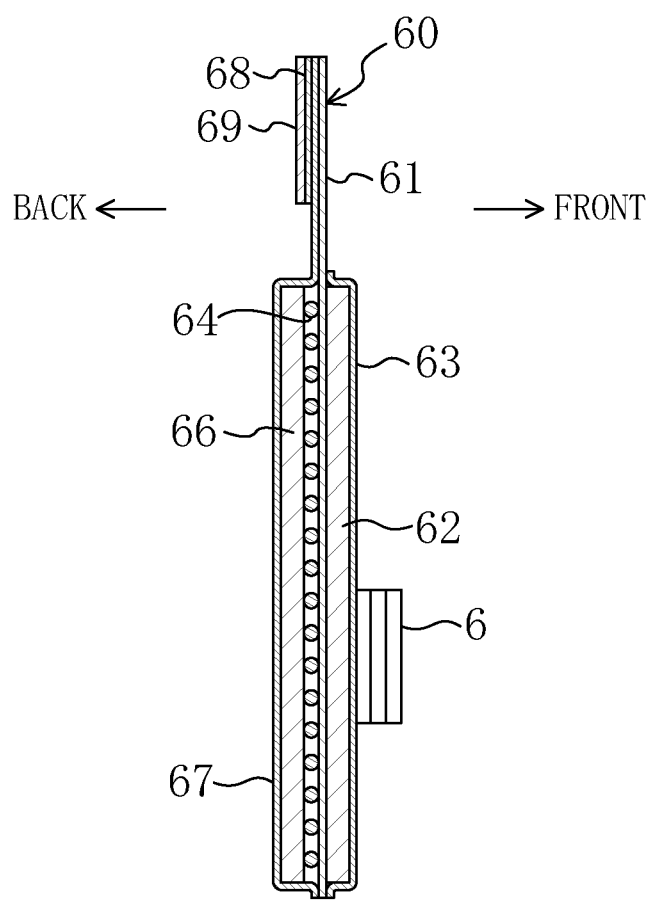
FIG. 22 is a cross-sectional view taken along the line XXII-XXII in FIG. 21.

Specifically, the auxiliary lighting units 6 do not each include a needle, and are attachable to the protectors 60. The protectors 60 are each configured to protect a wound region D (illustrated in FIG. 23) formed by incising body surface tissue in chest or abdominal surgery. As illustrated in FIG. 22, the protectors 60 each include an intermediate sheet 61 made of a resin, a first liquid absorbent material 62 placed on the front surface of the intermediate sheet 61, a first fabric material 63 configured so that the first liquid absorbent material 62 is held between the first fabric material 63 and the intermediate sheet 61, a base material 64 placed on the back surface of the intermediate sheet 61, a second liquid absorbent material 66, and a second fabric material 67 holding the second liquid absorbent material 66. An adhesive 68 and a release sheet 69 covering the adhesive 68 are provided on a region, which is apart from the base material 64, of the back surface of the intermediate sheet 61.

Figure 21:
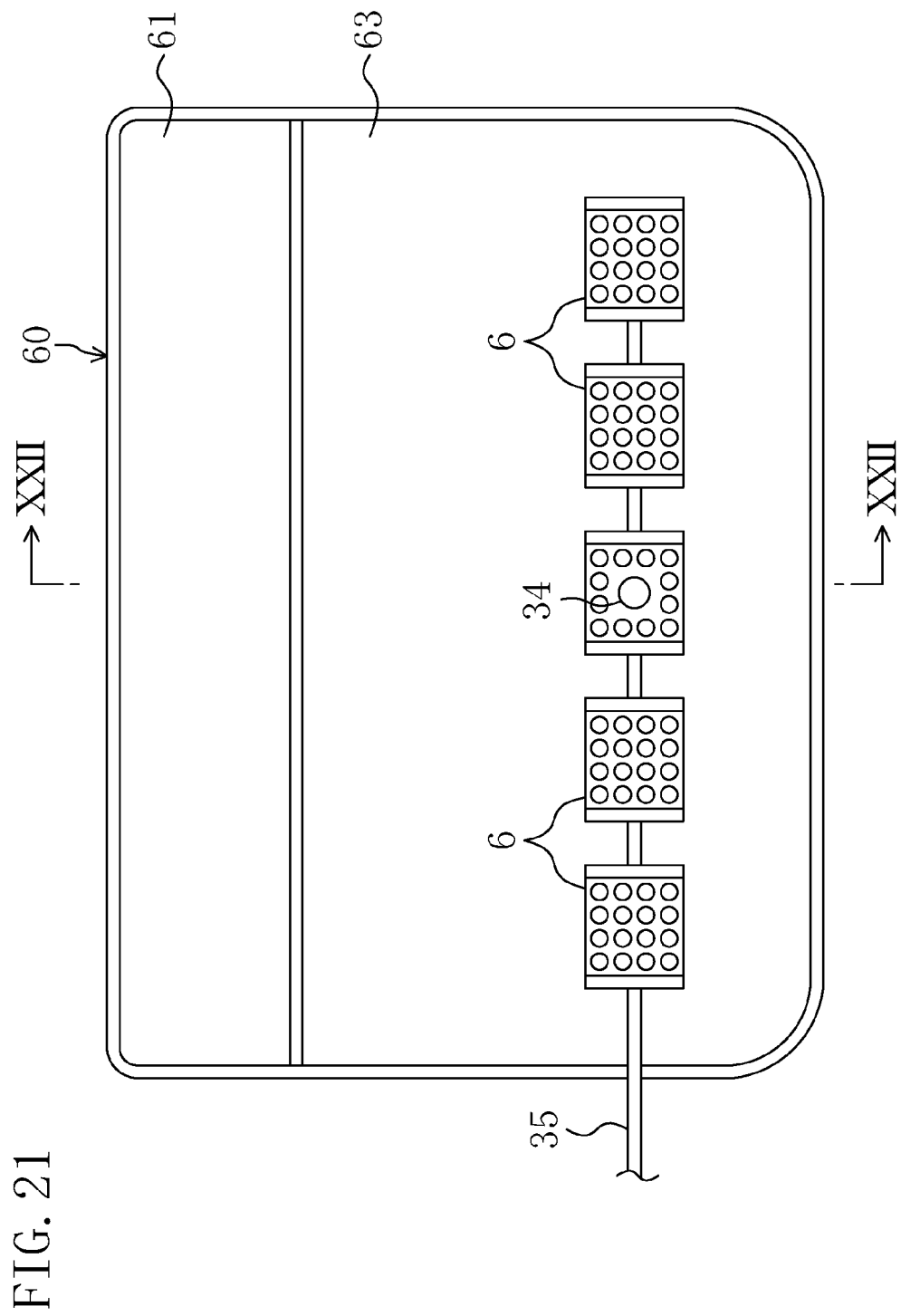
FIG. 21 is a front view of a protector and an auxiliary lighting unit according to the third embodiment.

The intermediate sheet 61 is made of a rectangular translucent film made of polyethylene. The longitudinal dimension of the intermediate sheet 61 is about 210 mm, and the width dimension thereof is about 150 mm. As illustrated in FIG. 21, the four corners of the intermediate sheet 61 are curved. The intermediate sheet 61 may be made of polyurethane, polyvinyl chloride, etc., and alternatively, may be made of a multilayer film obtained by stacking such resin materials.

The first liquid absorbent material 62 is made of water-swellable fiber. Lanseal which includes an inner layer of acrylic fiber and an outer layer of a water absorbent resin and which is made by TOYOBO CO., LTD. can be used as the water-swellable fiber. The speed at which the water-swellable fiber absorbs water corresponds to the speed under which, when the fiber is in contact with water, the fiber absorbs about 50% or more of the equilibrium water absorption in about 10 seconds. After the water-swellable fiber has absorbed water, the fiber is not separated from water even with the application of some pressure, and is insoluble in water. Moreover, while the fiber diameter of the water-swellable fiber after the absorption of water in the fiber increases to about five or more times the diameter of the fiber before the absorption of water therein, the longitudinal dimension of the fiber is maintained by the acrylic fiber, and thus, hardly varies before and after the absorption of water. The fiber properties of the water-swellable fiber are maintained by the acrylic fiber, and thus, are hardly degraded even when the outer layer, i.e., the water absorbent resin, absorbs water. The first liquid absorbent material 62 may be made of gauze of cotton, rayon, etc., and alternatively, may be made of a nonwoven fabric obtained by mixing water-swellable fiber into cotton or rayon, or a laminated body obtained by laminating water-swellable fiber on cotton or rayon.

The first fabric material 63 is made of a water-permeable nonwoven fabric. The nonwoven fabric forming the first fabric material 63 has heat sealing characteristics in which the nonwoven fabric is welded to the resin material by application of heat.

The adhesive 68 is provided near the back surface of the intermediate sheet 61. The adhesive 68 is an acrylic, silicone, polyurethane, or rubber adhesive typically used to adhere to human skin.

The release sheet 69 is obtained by undergoing a release process in which a silicone release agent is applied to a resin sheet, paper, etc. When the release sheet 69 is made of a resin sheet, for example, a polyethylene terephthalate film, a polypropylene film, etc., can be used. By contrast, when the release sheet 69 is made of paper, for example, glassine, clay-coated paper, laminated paper, etc., can be used.

The base material 64 is obtained by combining many wire rods made of a resin in a net-like configuration, and forms substantially the same shape as the first liquid absorbent material 62 when viewed in plan. The wire rods are each made of a shape-retaining resin material which, when bent, is not broken and retains the shape of the bent rod. For example, polyethylene, polypropylene, polyester, nylon, etc., can be used as the resin material. However, in this embodiment, out of the above resin materials, polyethylene having the best shape-retaining capability is used.

The second liquid absorbent material 66 and the second fabric material 67 are identical with the first liquid absorbent material 62 and the first fabric material 63, respectively.

Although not shown, the protectors 60 are each stored while being contained in a bag made of a resin film which is not moisture permeable together with paper for sterilization. This can prevent the first liquid absorbent material 62 and the second liquid absorbent material 66 from absorbing moisture in the air during storage, thereby preventing degradation in liquid absorption capacity.

As illustrated in FIGS. 20 and 21, the plurality of auxiliary lighting units 6, 6, . . . are adhered to the first fabric material 63 of each of the protectors 60. The auxiliary lighting units 6, 6, . . . are electrically connected together. The number of the auxiliary lighting units 6 may be one.

Figure 23:
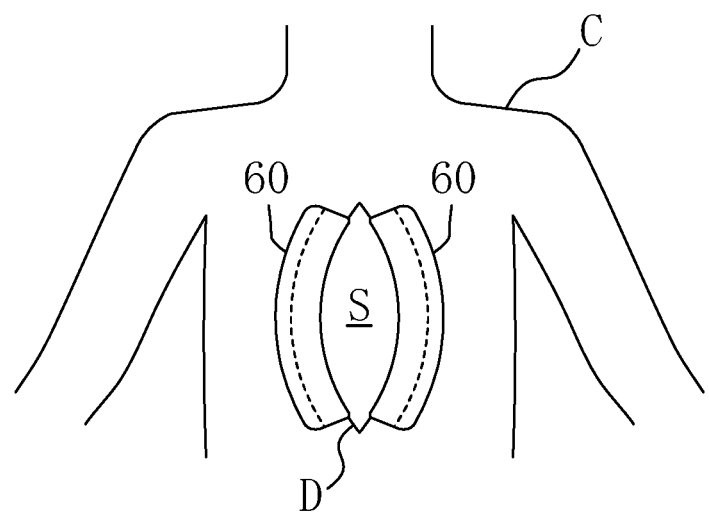
FIG. 23 is a diagram for explaining a situation where the protector and the auxiliary lighting unit according to the third embodiment are used.
Figure 24:
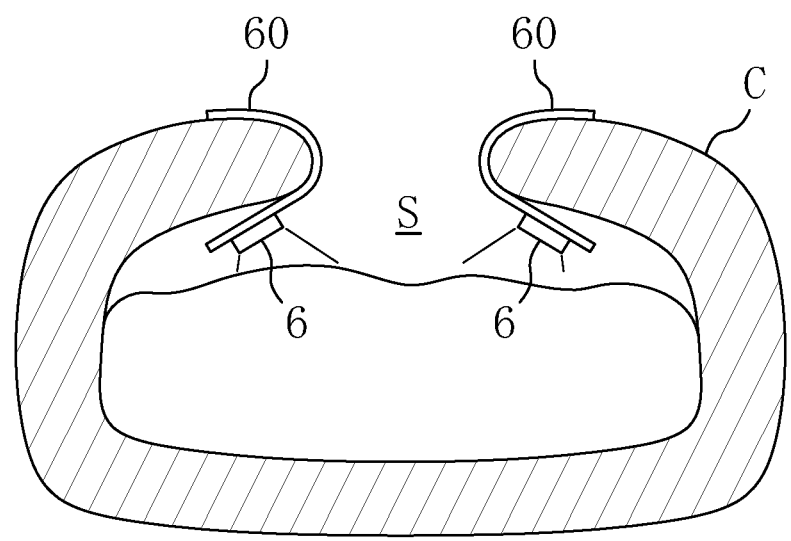
FIG. 24 is a diagram corresponding to FIG. 6 according to the third embodiment.

Next, a procedure for using the lighting system 1 according to the second embodiment will be described. As illustrated in FIGS. 23 and 24, after the wound region D has been opened, the protectors 60 are each oriented so that the second fabric material 67 is located near the wound region D, and then, are curved along the periphery of the wound region D, and the periphery of the wound region D is covered with the protectors 60. Subsequently, the release sheet 69 is separated from the adhesive 68, thereby bringing the adhesive 68 into intimate contact with a skin surface. Thus, the protectors 60 are less likely to move from the periphery of the wound region D, and furthermore, the auxiliary lighting units 6, 6, . . . are placed in the thoracic cavity or the abdominal cavity S.

Thereafter, when the auxiliary lighting units 6, 6, . . . are lighted by operating the switch 42 of the power supply 7, the interior of the thoracic cavity or the abdominal cavity S can be directly illuminated.

As described above, the periphery of the wound region D is covered with the protectors 60, and thus, pathogenic bacteria, etc., are less likely to adhere to the wound region D, thereby reducing the possibility of infection.

Blood emitted from the wound region D during surgery, body fluid oozing therefrom, etc., pass through the second fabric material 67, and are absorbed by the second liquid absorbent material 66.

The reference character 34 illustrated in FIG. 21 denotes a camera identical with the camera provided for each of the auxiliary lighting units 6 in the second variation of the first embodiment. A picture taken by the camera 34 is displayed on a monitor by radio communication or through a signal line. This enables observation of a deep portion of a body cavity which is difficult to be visually checked during surgery, thereby identifying a bleeding site, a focus, etc.

Therefore, according to the third embodiment, similar to the first embodiment, a necessary region can be illuminated at low cost without using a large-scale lighting system, such as a shadowless lamp, during surgery, and furthermore, the direction of light radiation can be changed as desired by the doctor A without causing dust, etc., to fall to the patient.

The auxiliary lighting units 6 are attached to the protectors 60, and thus, when the auxiliary lighting units 6 are fixed to the patient C, tissue of the patient C is not damaged, thereby allowing minimally invasive treatment.

The lighting system 1 of each of the first through third embodiments can be used also for surgical operations except the operations for the interior of the thoracic cavity or the abdominal cavity S, and can be also used during diagnosis or examinations.

Figure 25:
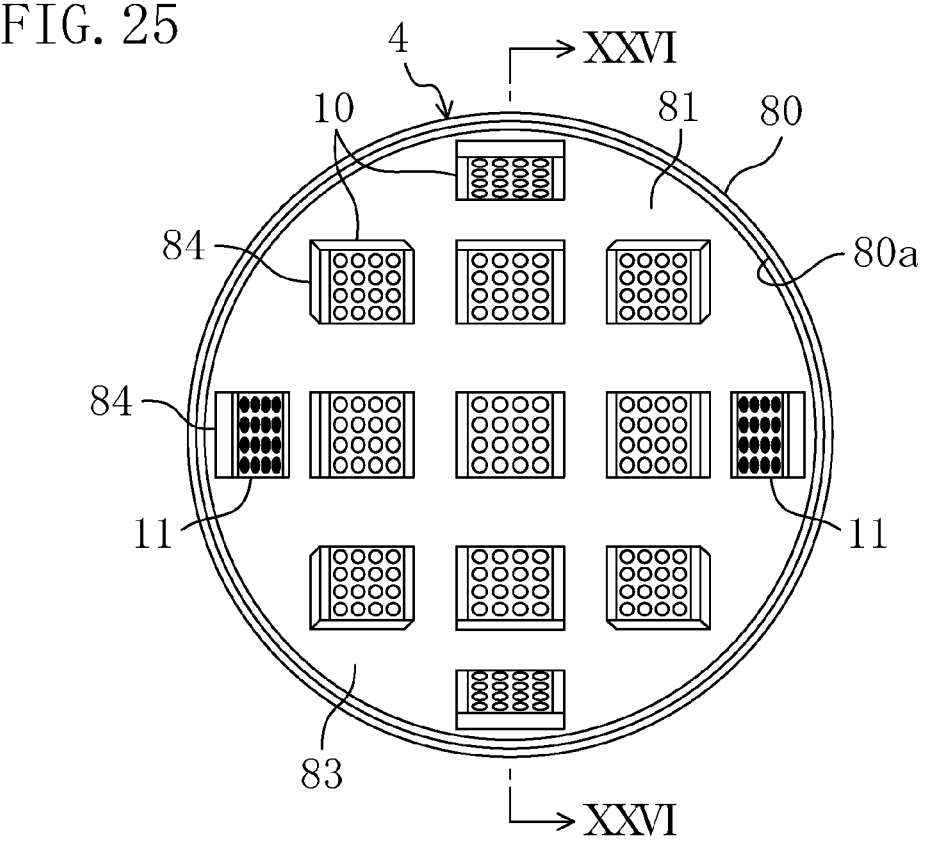
FIG. 25 is a diagram corresponding to FIG. 2 according to a first variation of the third embodiment.
Figure 26:
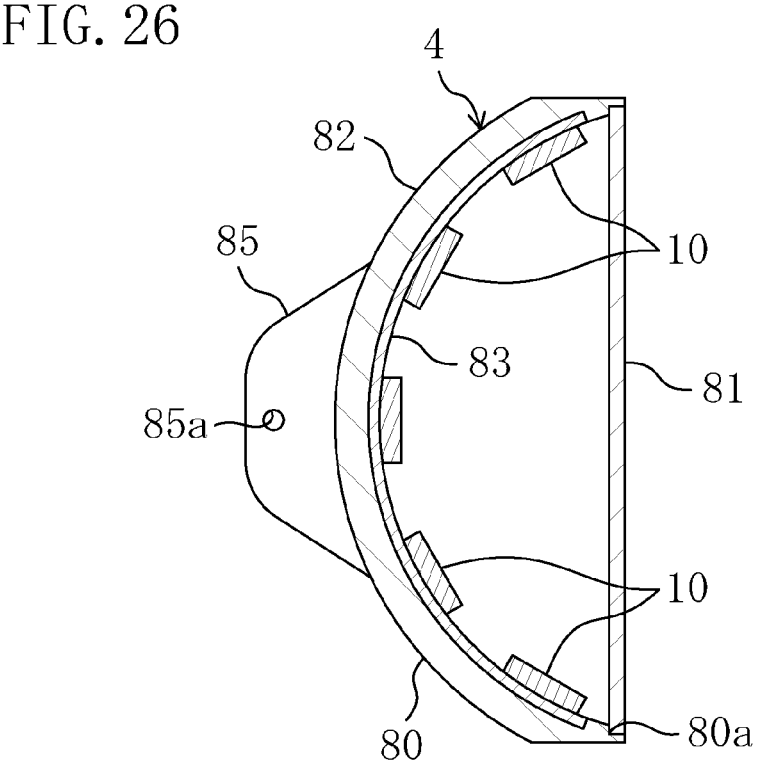
FIG. 26 is a cross-sectional view taken along the line XXVI-XXVI in FIG. 25.

The shape of the housing 13 of the light emitting unit 4 is not limited to a rectangular box shape, and as in a first variation illustrated in FIGS. 25 and 26, a housing 80 may form a circular shape when viewed from the front. A step 80a to which a lens 81 is fitted is formed at the edge of the opening of the housing 80. A board locking plate 82 is curved toward the (back) side of the housing 80 opposite to the lens 81 to thereby form a concave shape. An attachment board 83 is curved along the board locking plate 82 to thereby form a concave shape. The surface of the attachment board 83 is coated with a reflective material. The reference character 84 in FIG. 25 denotes connectors. The reference characters 85 and 85a in FIG. 26 denote side plates and through holes, respectively.

In the first variation, the white light emitting diode mounting boards 10 and the red light emitting diode mounting boards 11 are provided so that light is emitted to the center of the housing 80. This allows a central portion of an irradiated region to be brighter.

Figure 27:
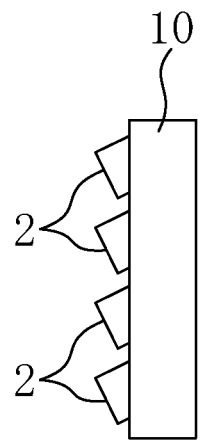
FIG. 27 is a diagram corresponding to FIG. 8 according to a second variation of the third embodiment.

As in the second variation illustrated in FIG. 27, the white light emitting diodes 2, 2, . . . may be provided so that the direction in which the white light emitting diodes 2, 2, . . . emit light is inclined relative to the corresponding white light emitting diode mounting boards 10. This can facilitate allowing the direction in which the white light emitting diodes 2, 2, . . . emit light to correspond to a desired direction. Other light emitting diodes can be also provided in a similar manner.

Figure 28:
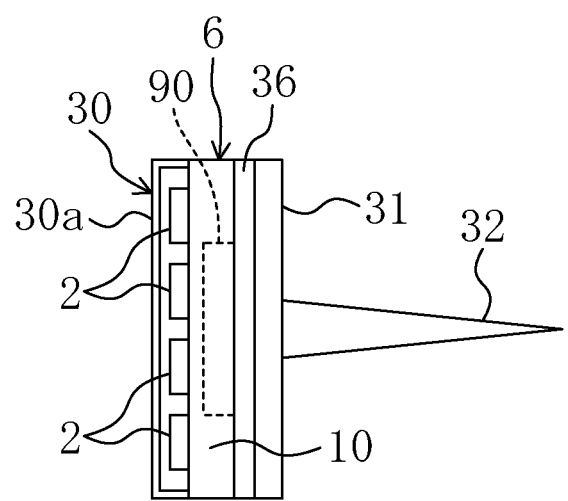
FIG. 28 is a diagram corresponding to FIG. 11 according to a third variation of the third embodiment.

As in a third variation illustrated in FIG. 28, the auxiliary lighting units 6 may each include a battery 90. This eliminates the need for power cords for the auxiliary lighting units 6. The battery 90 may be exchangeable, or may be unexchangeable. The battery 90 may be a rechargeable battery.

Figure 29:
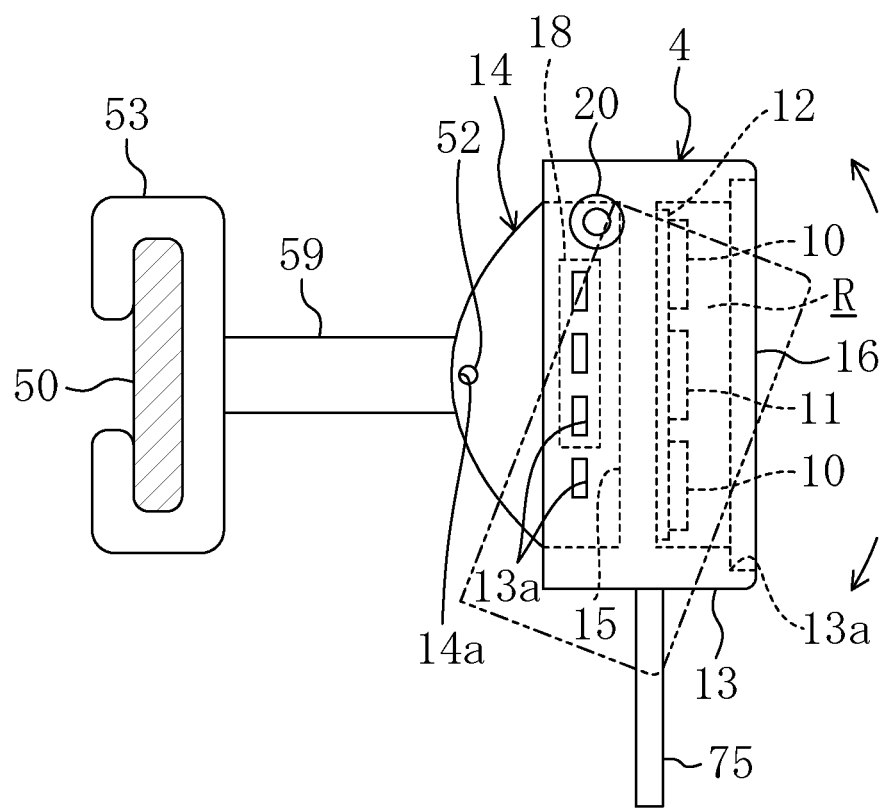
FIG. 29 is a diagram corresponding to FIG. 3 according to a fourth variation of the third embodiment.

As in a fourth variation illustrated in FIG. 29, the support member 53 may be apart from the light emitting unit 4. Specifically, the support member 53 includes a rod 59 protruding from the front face of the support member 53. The spindle 52 is provided towards the distal end of the rod 59. The spindle 52 is inserted through the through holes 14a of the light emitting unit 4. When, as in the fourth variation, the light emitting unit 4 is apart from the support member 53, the range in which the light emitting unit 4 is movable is less likely to be limited by the support member 53, thereby increasing the range in which the light emitting unit 4 is movable. Heat of the light emitting diodes 2 and 3 generated by the light emitting unit 4 is less likely to be transferred to the doctor A.

In the fourth variation, an operating rod 75 is detachably attached to the light emitting unit 4. The operating rod 75 is attached to the light emitting unit 4 by being screwed into a screw hole (not shown) formed in the light emitting unit 4 or being inserted into an insertion hole (not shown) formed in the light emitting unit 4. The doctor A can easily change the angle of the light emitting unit 4 with the operating rod 75. When the operating rod 75 is removed from the light emitting unit 4 after the change of the angle, the operating rod 75 does not obstruct a procedure. The operating rod 75 is preferably sterilized. The operating rod 75 is preferably attached to the bottom of the light emitting unit 4. However, the operating rod 75 may be attached to the top of the light emitting unit 4. The left light emitting diode attachment member 4b and the right light emitting diode attachment member 4c of the second embodiment can each include the operating rod 75.

The auxiliary lighting units 6 can be sold while being packaged separately from the light emitting unit 4 and the securing member 5.

The light emitting unit 4 may include an inclination sensor for sensing an inclination, and a controller for controlling the light emitting diodes 2 and 3, and the light emitting diodes 2 and 3 may be controlled based on an output signal from the inclination sensor. Specifically, when the doctor A conducts a procedure while facing downward, the light emitting diodes 2 and 3 are lighted, and by contrast, when the doctor A faces forward or faces upward, some or all of the light emitting diodes 2 and 3 may be turned off, and alternatively, light from the lighted light emitting diodes 2 and 3 may be darkened. This can reduce glare felt by a person who is located to the front of the doctor A, and can reduce battery exhaustion.

A shutter may be provided on the front face of the light emitting unit 4, and the shutter may be controlled based on an output signal from the inclination sensor. Specifically, when the doctor A conducts a procedure while facing downward, the shutter is controlled to prevent the shutter from covering the light emitting unit 4. By contrast, when the doctor A faces forward or faces upward, the shutter covers the entire front face of the light emitting unit 4 or part of the front face.

In the above embodiments, the light emitting unit 4 includes the light emitting diodes 2 and 3. However, this is not restrictive, and for example, the light emitting unit 4 may include discharge lamps, etc.

INDUSTRIAL APPLICABILITY

As described above, the lighting system according to the present invention can be used for surgery for the interior of, e.g., a thoracic cavity or an abdominal cavity.

DESCRIPTION OF REFERENCE CHARACTERS

1 LIGHTING SYSTEM
2 WHITE LIGHT EMITTING DIODE
3 RED LIGHT EMITTING DIODE
4 LIGHT EMITTING UNIT
5 SECURING MEMBER
6 AUXILIARY LIGHTING UNIT
7 POWER SUPPLY
10 WHITE LIGHT EMITTING DIODE MOUNTING BOARD
11 RED LIGHT EMITTING DIODE MOUNTING BOARD
23 CONNECTOR
32 NEEDLE
55, 56 HINGE MECHANISM (ILLUMINATION ANGLE CHANGER)
60 PROTECTOR
A DOCTOR
C PATIENT
S THORACIC CAVITY OR ABDOMINAL CAVITY
D WOUND REGION

The invention claimed is:

1. A lighting system comprising:
a securing unit having a head band adapted to be secured to the head of a healthcare worker;
a main body fixed to the securing unit, and having a planar illuminating surface to which a light emitting diode configuring to illuminate an operative field of a patient during surgery is attached;
a left lighting unit which has a planar illuminating surface and a plurality of light emitting diodes on the planar illuminating surface, is coupled directly to the main body and shares a first single-hinge mechanism having a vertically extending rotation axis to a portion of the main body, and is adapted to be located to a left side of the healthcare worker, and to which a light emitting diode configured to illuminate the operative field of the patient during surgery is attached; and
a right lighting unit which has a planar illuminating surface and a plurality of light emitting diodes on the planar illuminating surface, is coupled directly to the main body and shares a second single-hinge mechanism having a vertically extending rotation axis to a portion of the main body, and is adapted to be located to a right side of the healthcare worker, and to which a light emitting diode configured to illuminate the operative field of the patient during surgery is attached; wherein:
the left and right lighting units move relatively closer to each other or relatively further apart from each other by a rotation of each of the left and right lighting units about rotation axes of the corresponding first or second single hinge mechanisms;

the illuminating surface of the left lighting unit and the illuminating surface of the main body are closely coupled with no gap therebetween along the first single-hinge mechanism, the illuminating surface of the main body and the illuminating surface of the right lighting unit are closely coupled with no gap therebetween along the second single-hinge mechanism, and the illuminating surfaces of the left lighting unit, the main body and the right lighting unit form a bended and still unified surface; and even under a condition that degrees of angles differ from each other by rotations of the left lighting unit and the right lighting unit, the illuminating surface of the left lighting unit, the illuminating surface of the main body and the illuminating surface of the right lighting unit are maintained coupled with no gap therebetween, and light illuminated from the illuminating surfaces illuminates the operative field of the patient by reflecting the light.

2. The lighting system of claim 1, wherein the first single-hinge mechanism and the second single-hinge mechanism are configured to lock to prevent the left lighting unit and the right lighting unit from unintentionally moving.

3. A lighting system adapted to be secured to the head of a healthcare worker, comprising:

a securing unit having a head band adapted to be secured to the head of a healthcare worker;

a left lighting unit located at the left side of the head of the healthcare worker, fixed to the securing unit, and having a planar illuminating surface to which a plurality of light emitting diodes configured to illuminate an operative field of a patient during surgery are attached;

a right lighting unit located at the right side of the head of the healthcare worker; fixed to the securing unit, and having a planar illuminating surface to which a plurality of light emitting diodes configured to illuminate the operative field of the patient during surgery are attached; and, a hinge mechanism which is shared by and directly connects to the left lighting unit and right lighting unit, wherein:

the hinge mechanism has a vertically extending rotation axis;

the left and right lighting units move relatively closer to each other or relatively further apart from each other by a rotation of each of the left and right lighting units about a rotation axis of the hinge mechanism;

the illuminating surface of the left lighting unit and the illuminating surface of the right illuminating unit are directly coupled so as to form a bended and still unified surface; and even under a condition that degrees of angles differ from each other by rotations of the left lighting unit and the right lighting unit, the illuminating surface of the left lighting unit and the illuminating surface of the right lighting unit are maintained coupled with no gap therebetween, and light illuminated from the illuminating surfaces illuminates the operative field of the patient by reflecting the light.

4. The lighting system of claim 3, wherein the hinge mechanism configured to lock to prevent the left and right lighting units from unintentionally moving.

* * * * *